(12) United States Patent
Aklog et al.

(10) Patent No.: US 9,155,834 B2
(45) Date of Patent: Oct. 13, 2015

(54) SYSTEMS AND METHODS FOR INFUSION OF FLUIDS USING STORED POTENTIAL ENERGY AND A VARIABLE FLOW RESISTOR

(71) Applicant: Pavilion Holdings Group LLC, Norwell, MA (US)

(72) Inventors: Lishan Aklog, Scottsdale, AZ (US); Brian Justo deGuzman, Paradise Valley, AZ (US); Michael Glennon, Norwell, MA (US); Paul John Cronin, Allen, TX (US); William Edgar Barker, Lewisville, TX (US)

(73) Assignee: Pavilion Holdings Group, LLC, Norwell, MA (US)

( * ) Notice: Subject to any disclaimer, the term of this patent is extended or adjusted under 35 U.S.C. 154(b) by 0 days.

(21) Appl. No.: 14/094,046

(22) Filed: Dec. 2, 2013

(65) Prior Publication Data
US 2014/0083529 A1    Mar. 27, 2014

Related U.S. Application Data

(62) Division of application No. 13/041,296, filed on Mar. 4, 2011, now Pat. No. 8,622,976.

(60) Provisional application No. 61/310,601, filed on Mar. 4, 2010.

(51) Int. Cl.
*A61M 5/00* (2006.01)
*A61M 5/178* (2006.01)
(Continued)

(52) U.S. Cl.
CPC ......... *A61M 5/16877* (2013.01); *A61M 5/1452* (2013.01); *A61M 5/14593* (2013.01); *A61M 5/16804* (2013.01); *A61M 5/16813* (2013.01); *A61M 2205/60* (2013.01)

(58) Field of Classification Search
CPC . A61M 1/0056; A61M 5/31511; A61M 5/36; A61M 2005/3123; A61M 2005/31516; A61M 5/1407; A61M 5/1408; A61M 5/1409; A61M 5/16877; A61M 5/1452; A61M 5/14593; A61M 5/16804; A61M 5/16813; A61B 5/150213; A61B 5/150221
USPC .............. 604/184, 186, 190, 85, 89, 91, 207, 604/215, 221, 246, 236, 167.01, 167.06, 604/118, 121
See application file for complete search history.

(56) References Cited

U.S. PATENT DOCUMENTS

| | | | |
|---|---|---|---|
| 4,573,994 | A | 3/1986 | Fischell et al. |
| 5,100,389 | A | 3/1992 | Vaillancourt |

(Continued)

OTHER PUBLICATIONS

Office Action issued for U.S. Appl. No. 13/041,296 mailed Feb. 4, 2013.

(Continued)

*Primary Examiner* — Theodore Stigell
*Assistant Examiner* — Lauren M Peng
(74) *Attorney, Agent, or Firm* — Greenberg Traurig, LLP; Chinh H. Pham; Roman Fayerberg

(57) ABSTRACT

Systems and methods for infusion of fluids using stored potential energy and a variable flow resistor. In one aspect of the present disclosure, there is provided an infusion device that includes a plunger situated within a vessel so as to define a chamber within which a volume of fluid can be accommodated between a downstream surface of the plunger and the vessel. The infusion device further includes an outflow path through which the fluid in the chamber can be dispensed upon displacement of the plunger by a force acting thereon. A variable flow resistor is situated within the outflow path and is configured to allow a substantially constant fluid flow rate from the vessel to be maintained as the force acting on the plunger decreases.

4 Claims, 39 Drawing Sheets

(51) Int. Cl.
*A61M 5/315* (2006.01)
*A61M 5/168* (2006.01)
*A61M 5/145* (2006.01)

(56) References Cited

U.S. PATENT DOCUMENTS

| | | |
|---|---|---|
| 5,800,405 A | 9/1998 | McPhee |
| 2003/0040709 A1 | 2/2003 | Mason |
| 2007/0066939 A1* | 3/2007 | Krulevitch et al. ........... 604/152 |
| 2008/0154240 A1 | 6/2008 | Shippert |
| 2009/0088724 A1* | 4/2009 | Chebator et al. .............. 604/508 |

OTHER PUBLICATIONS

International Search Report and Written Opinion for International Application No. PCT/US2011/027298 Mailed Apr. 29, 2011.

* cited by examiner

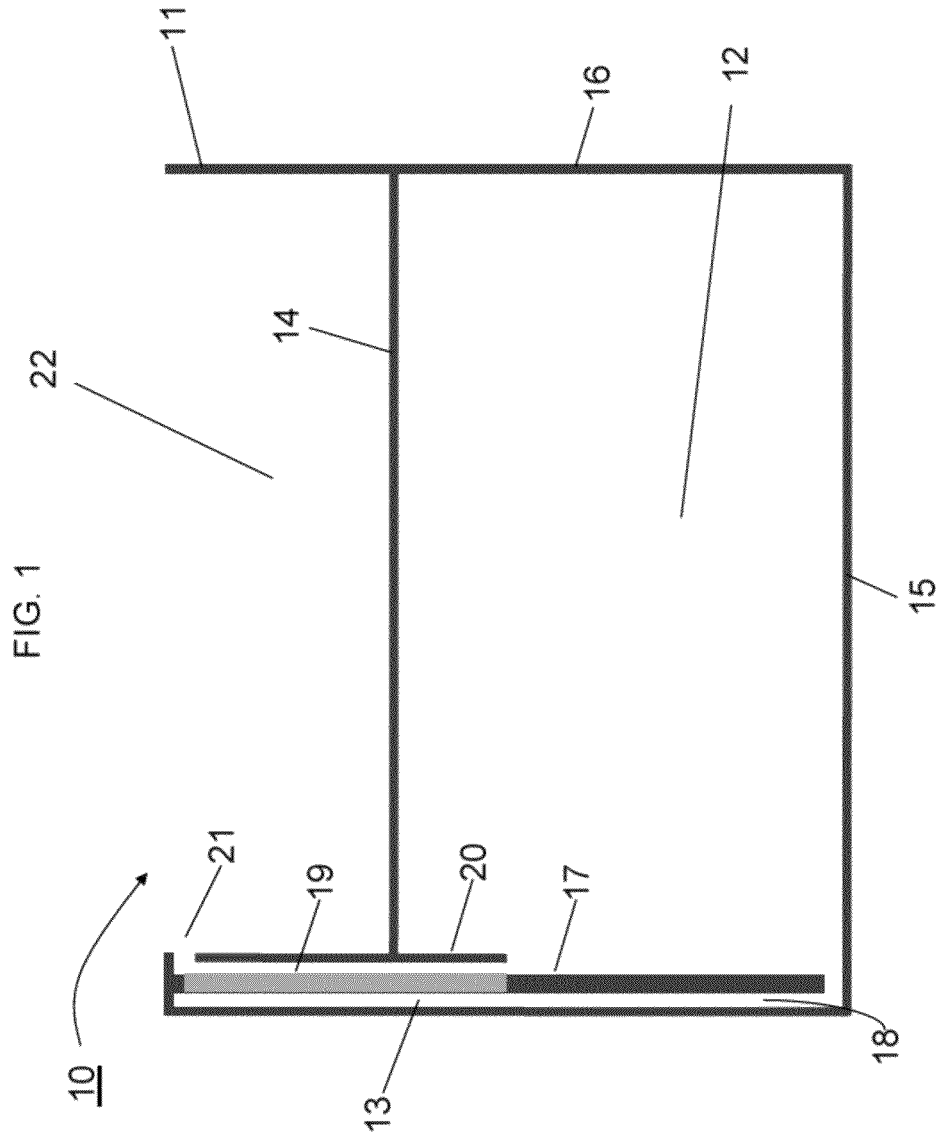

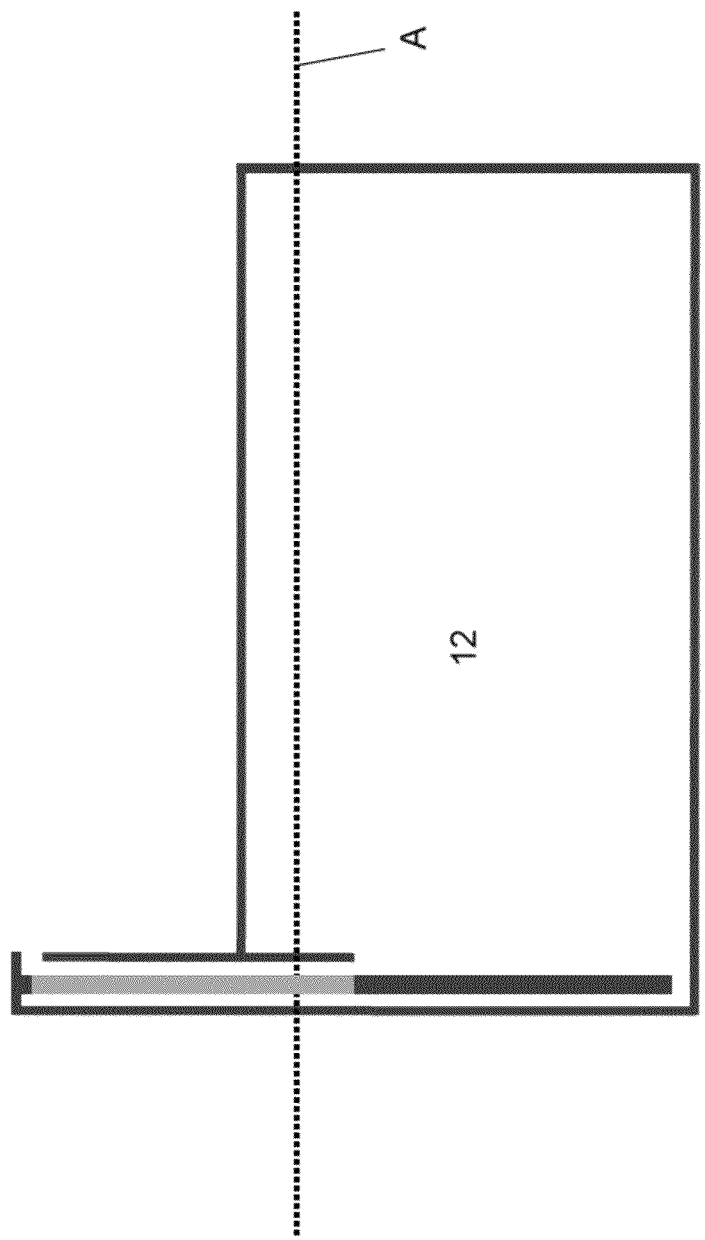

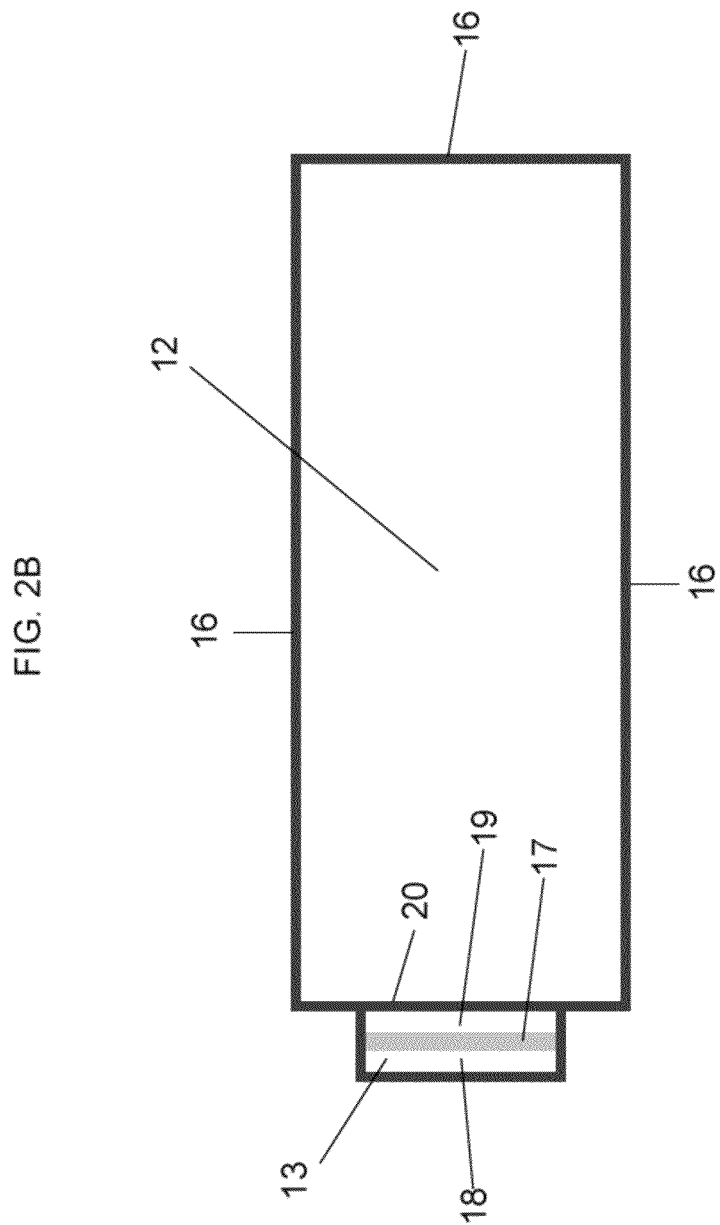

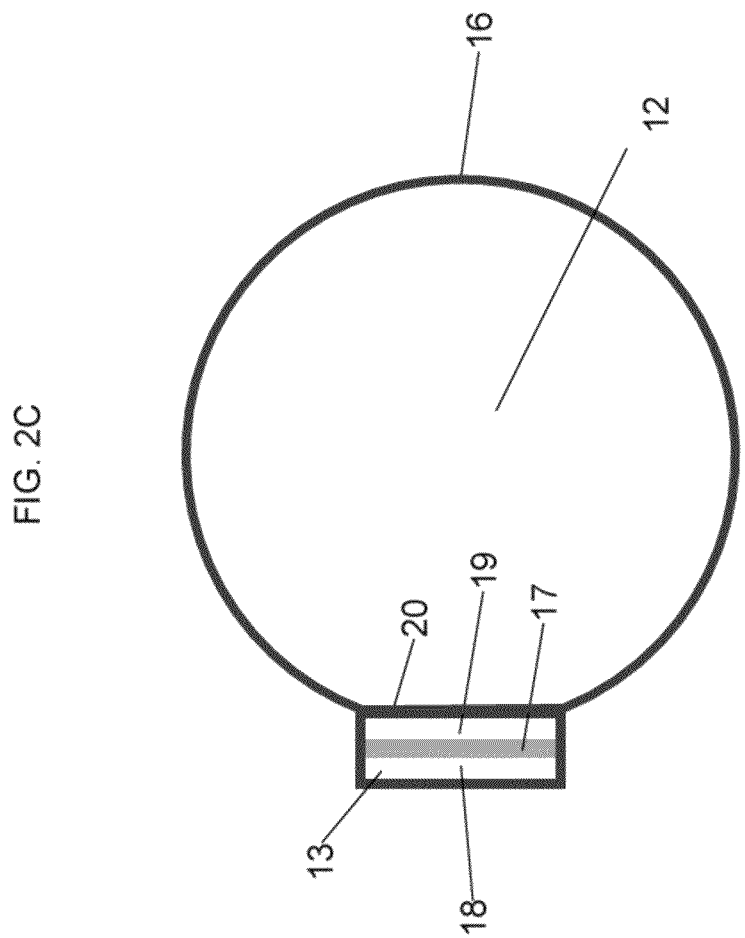

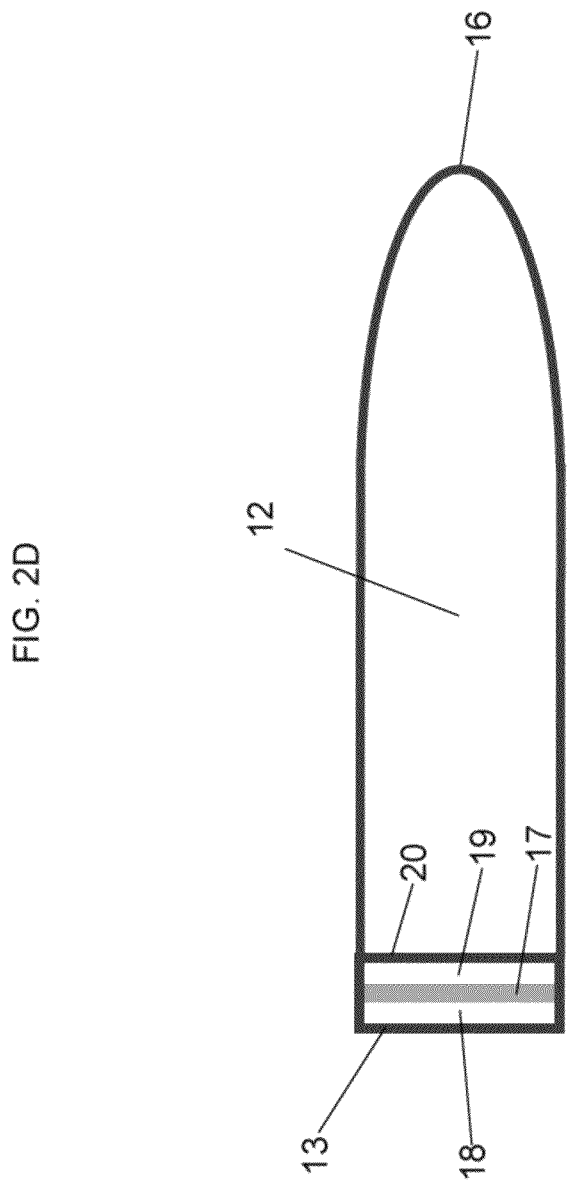

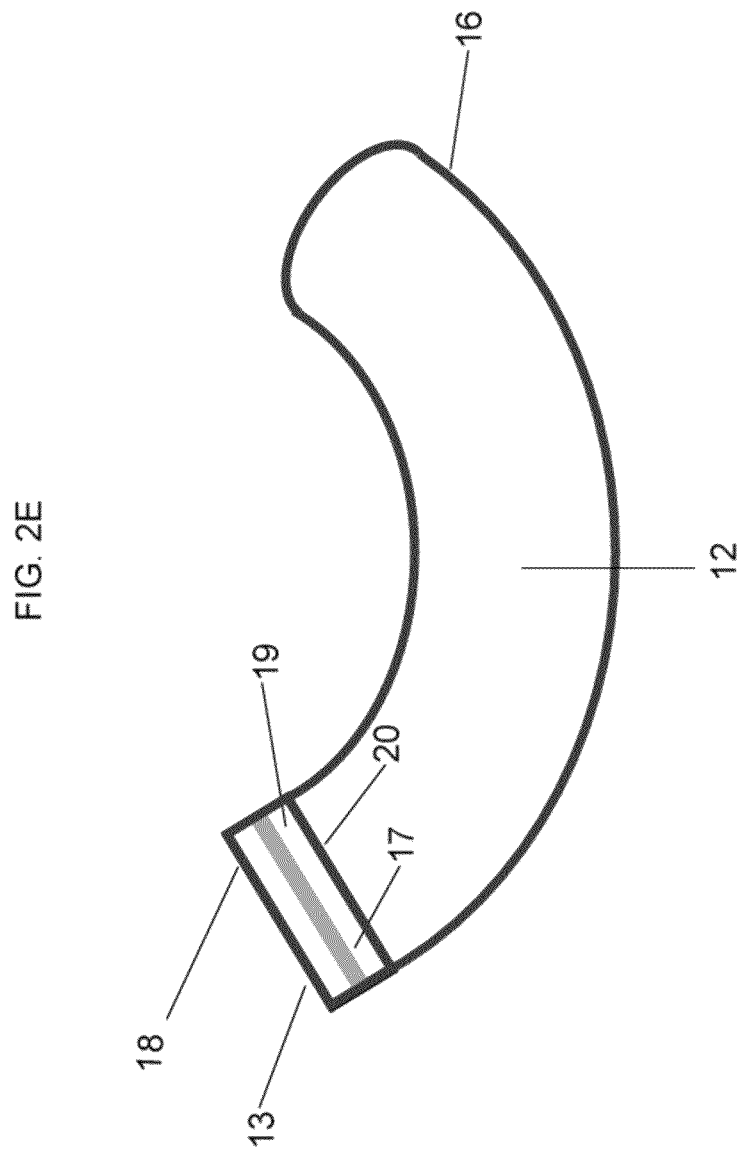

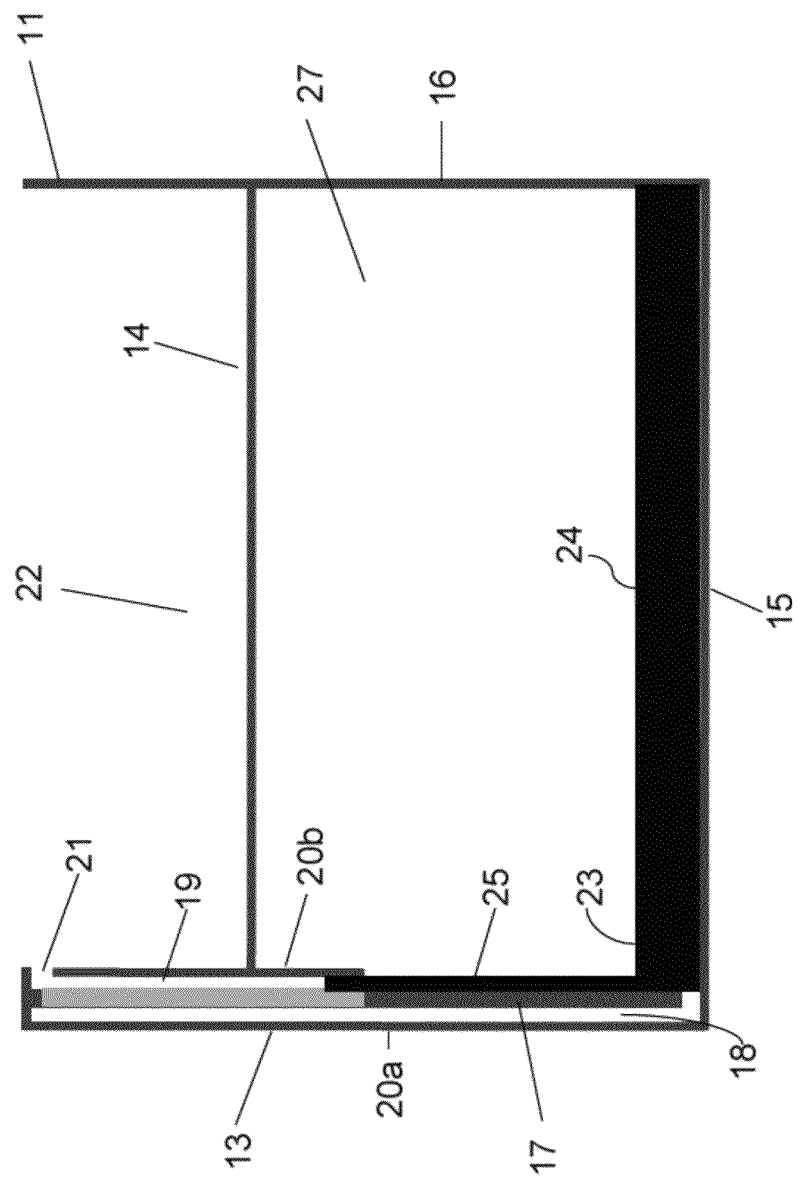

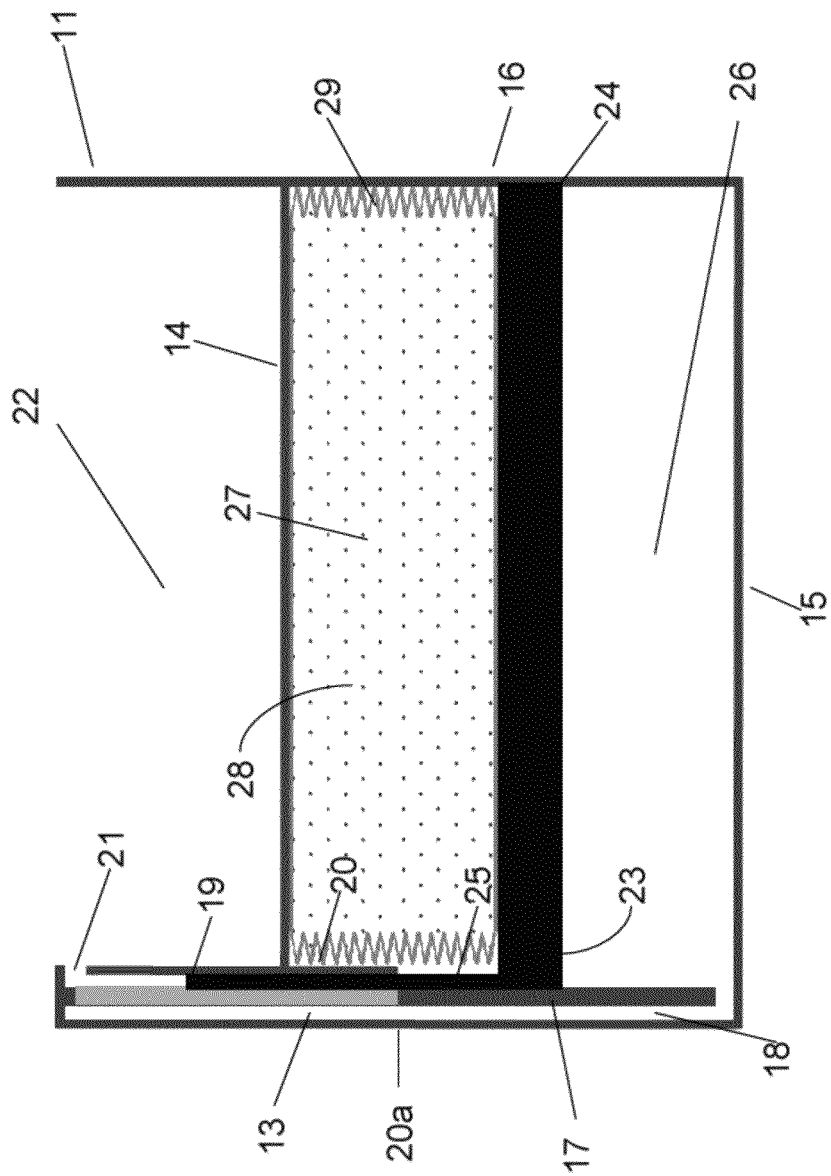

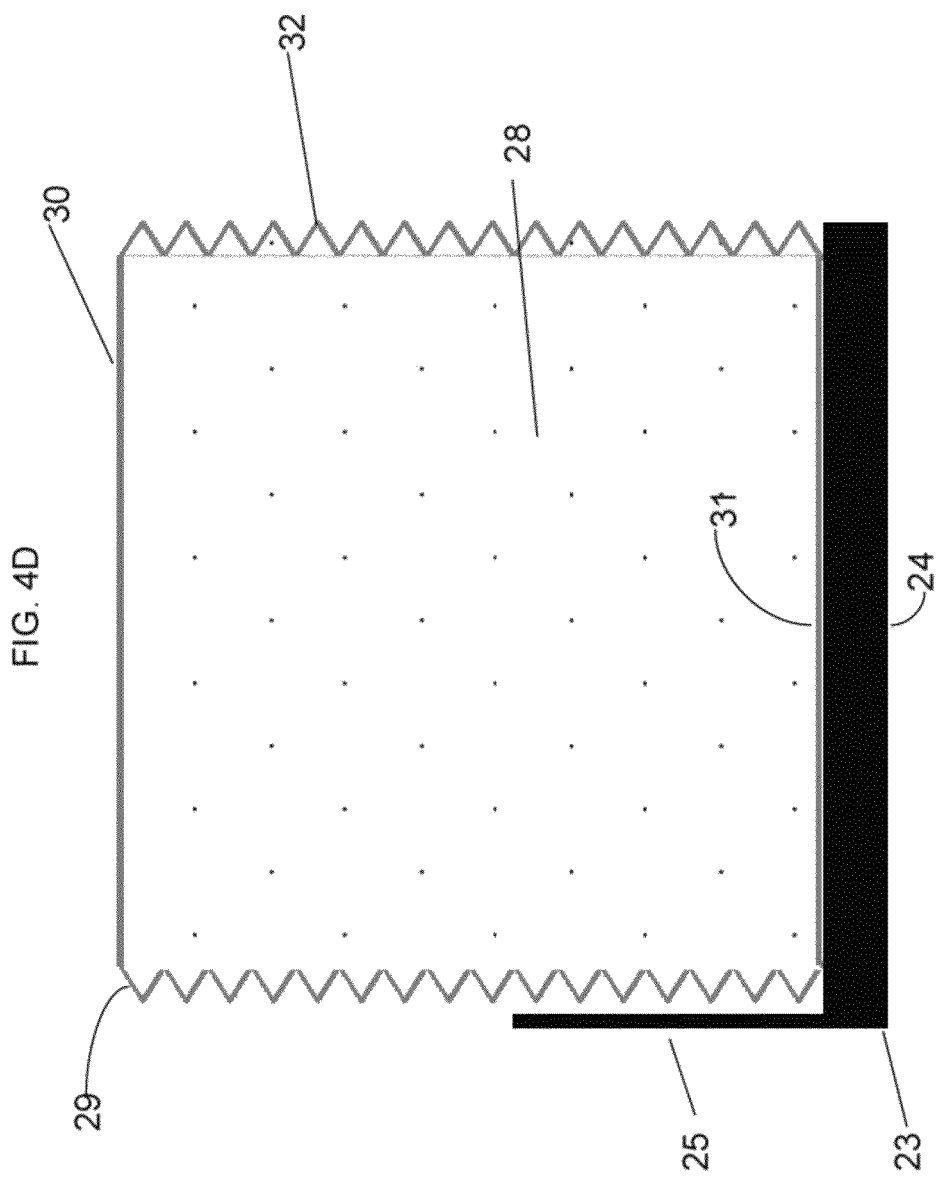

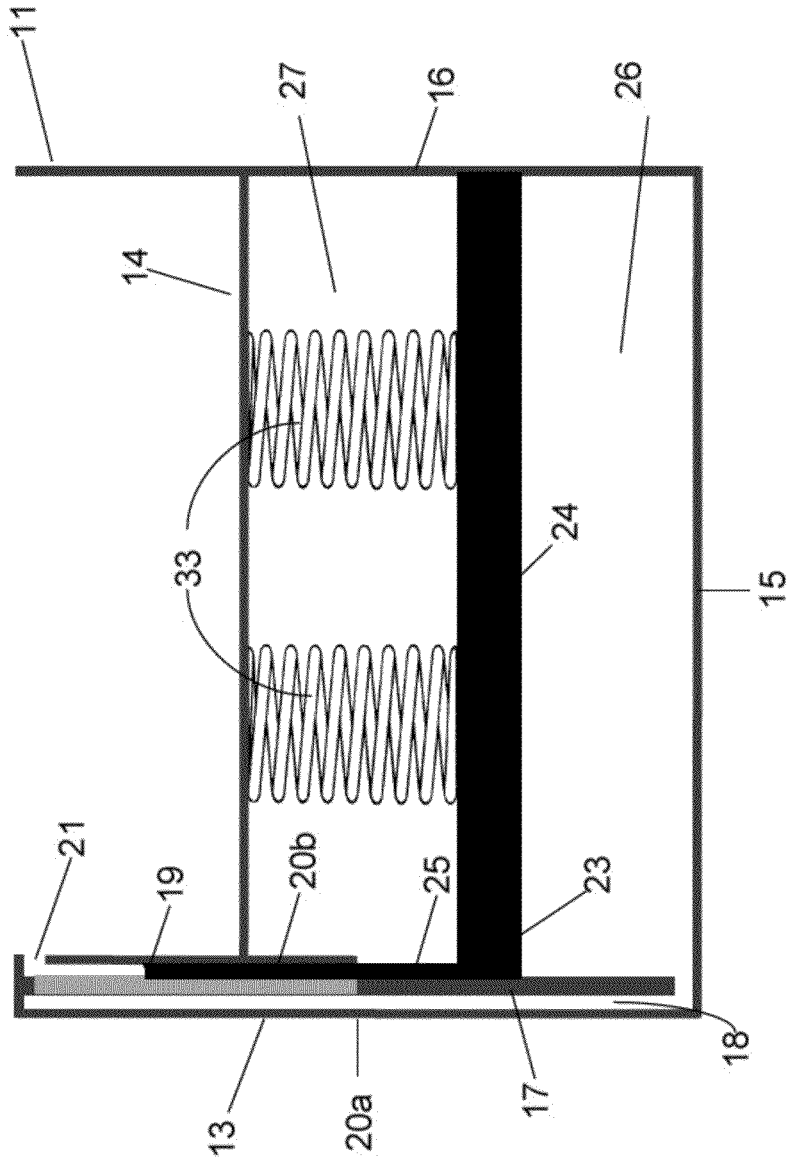

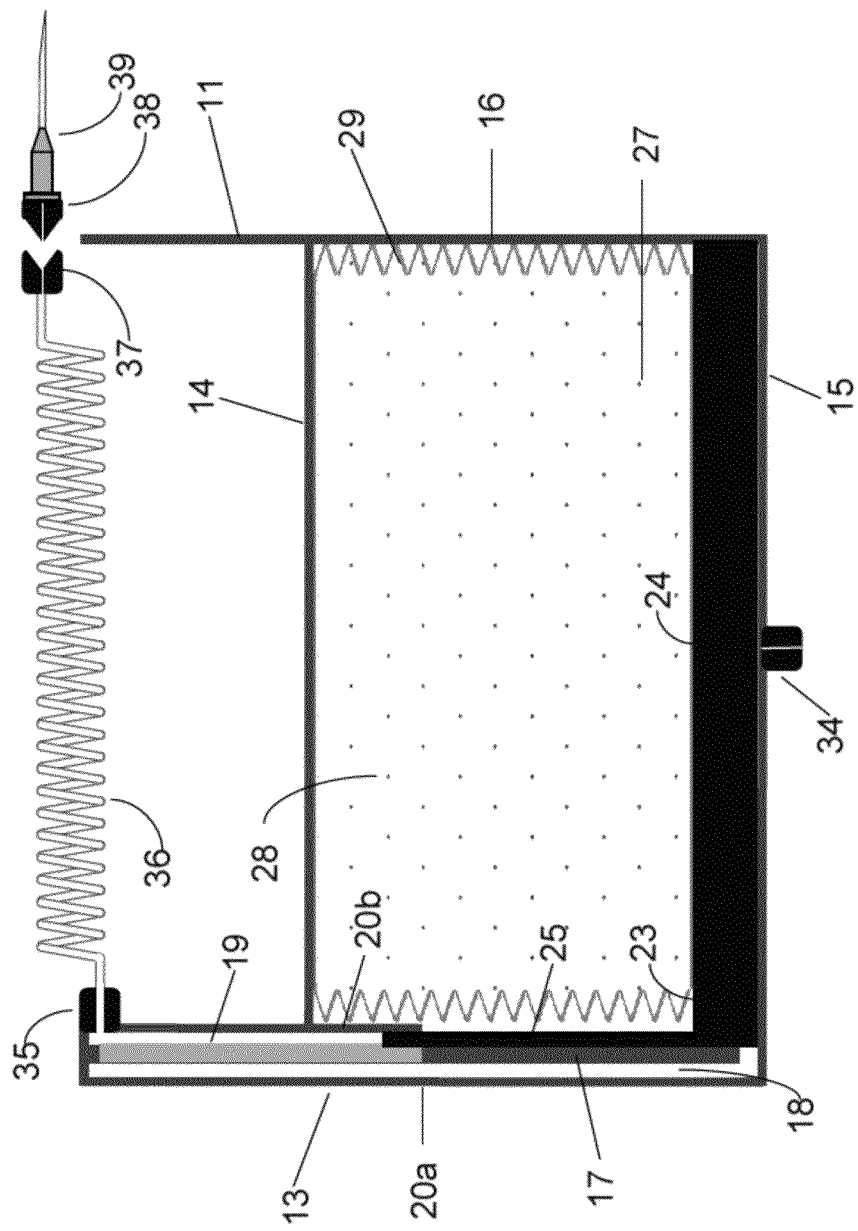

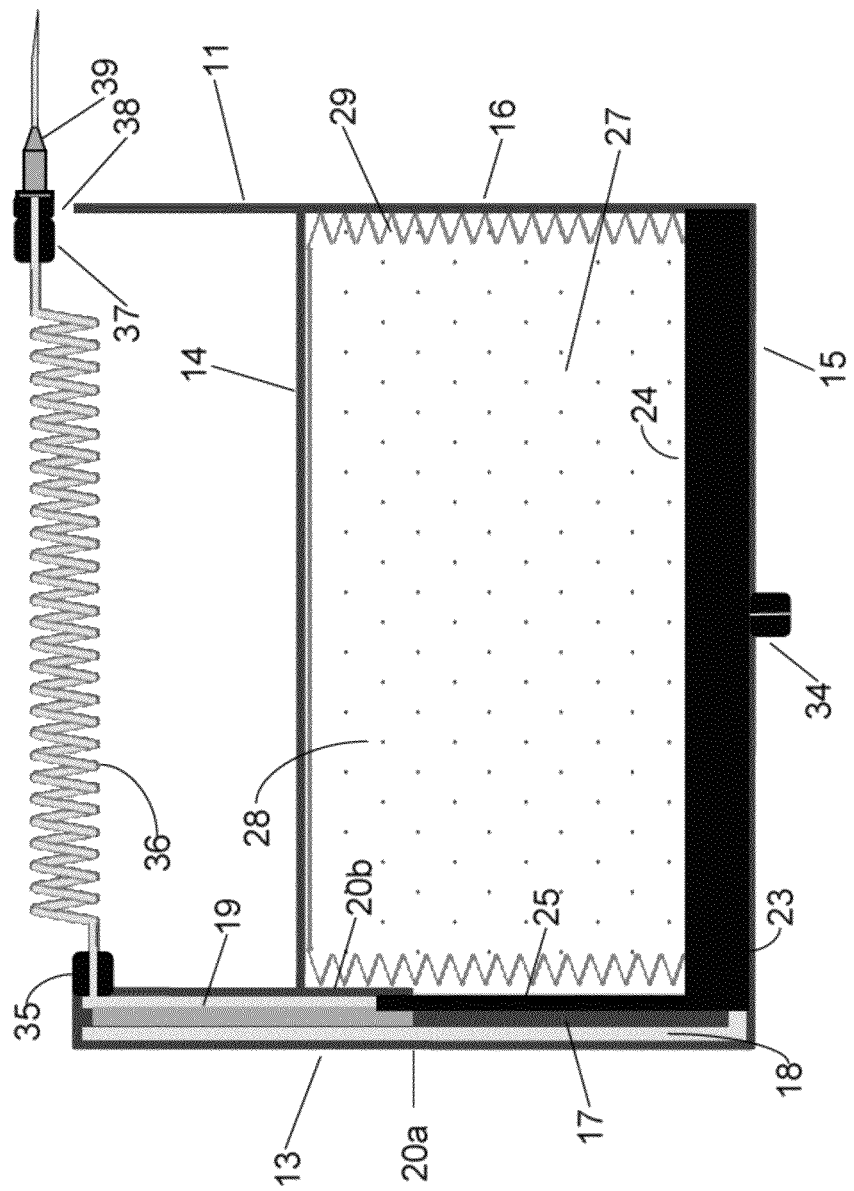

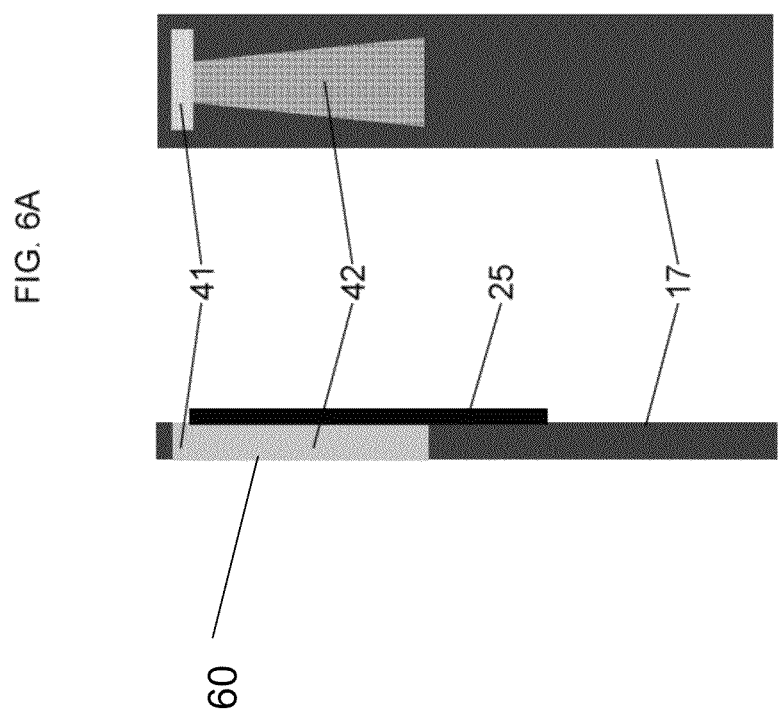

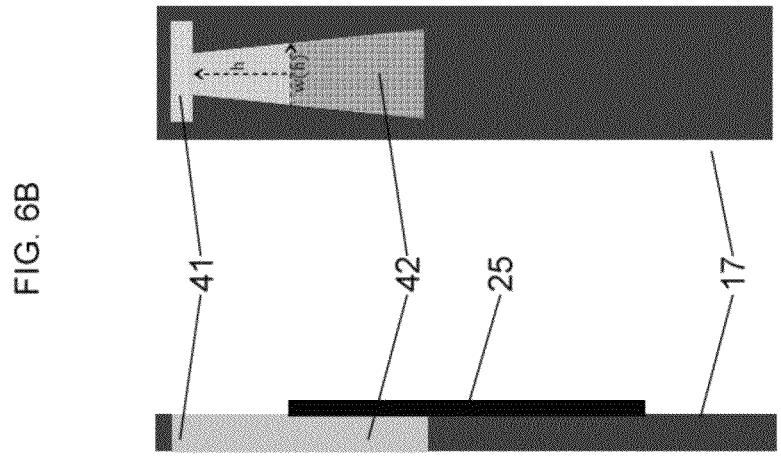

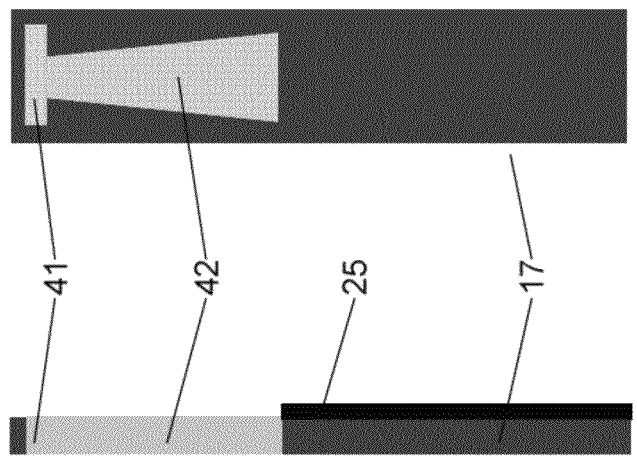

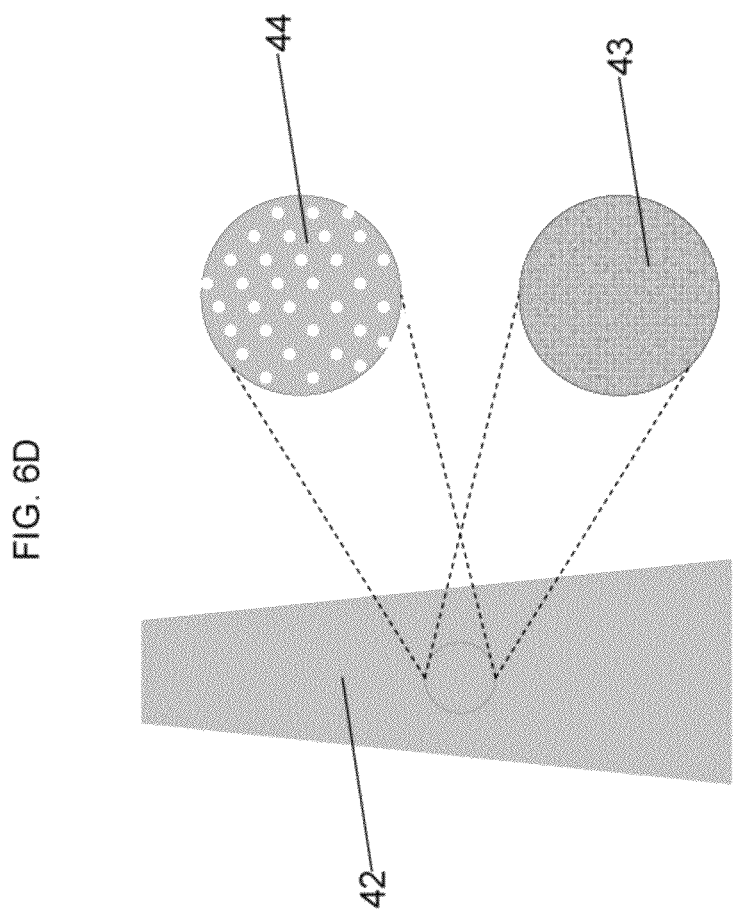

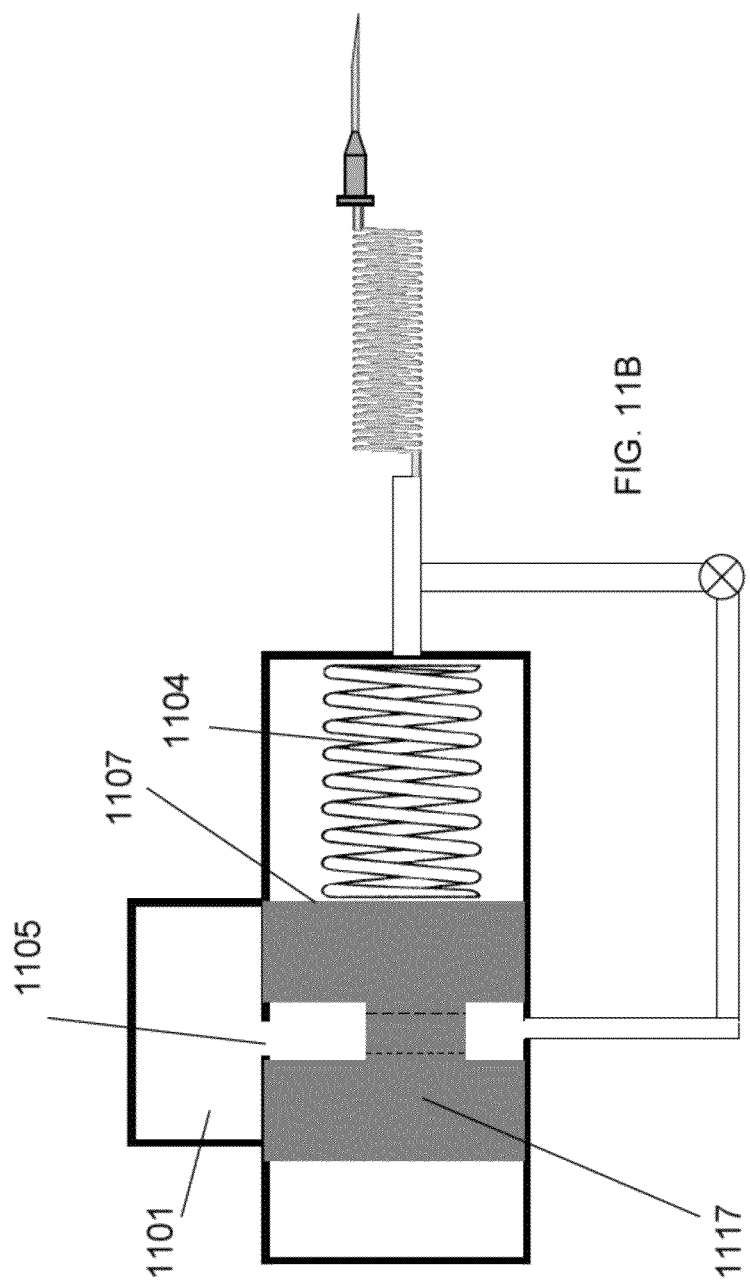

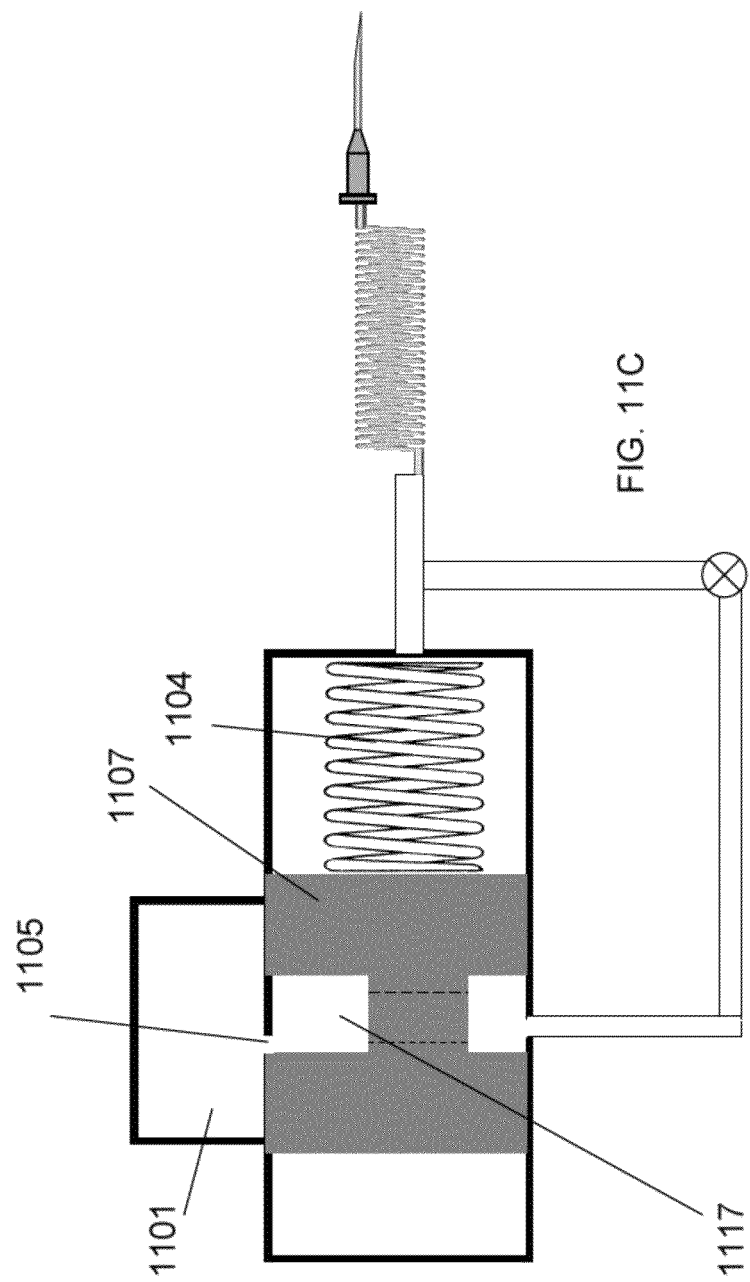

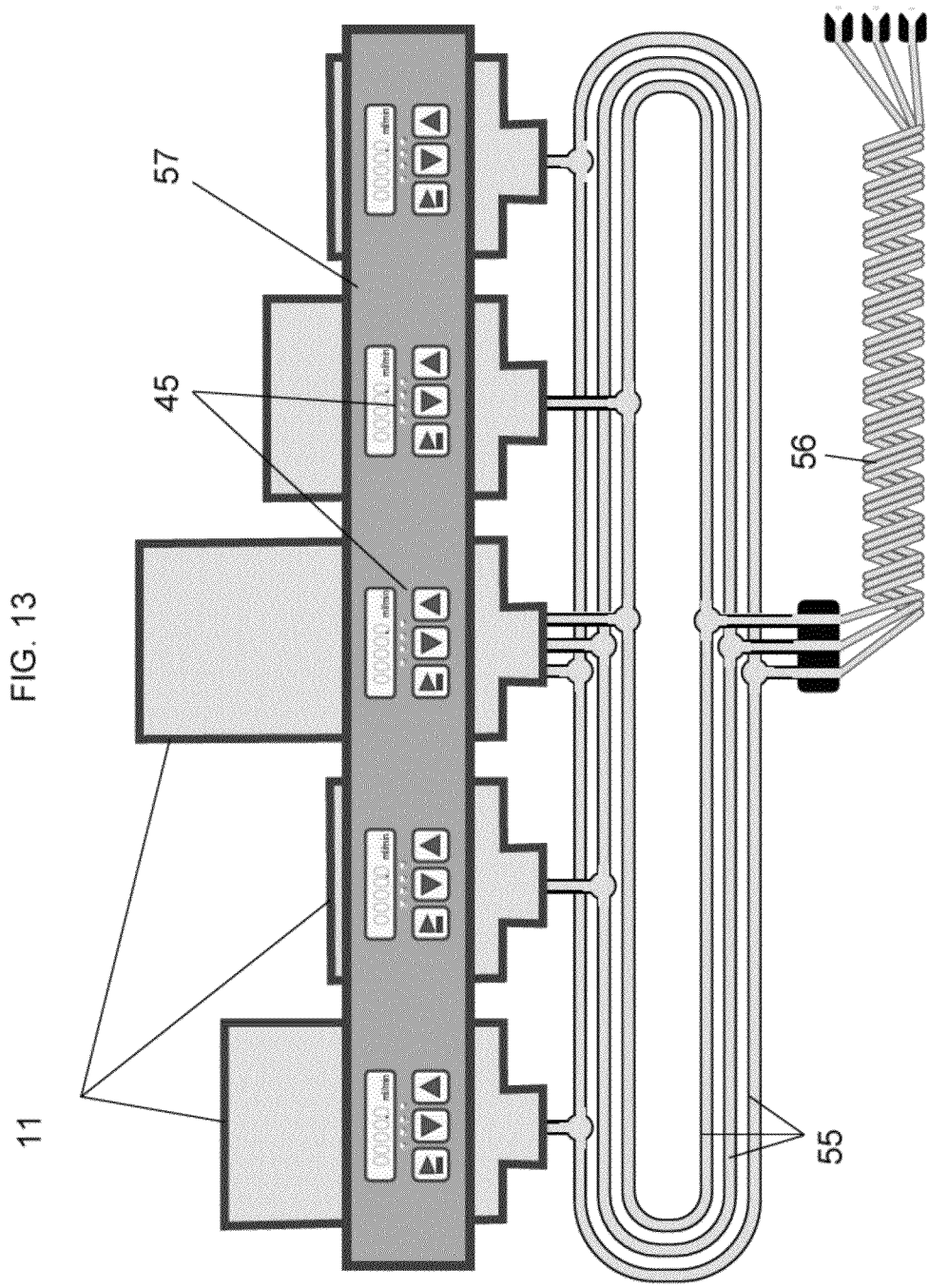

SYSTEMS AND METHODS FOR INFUSION OF FLUIDS USING STORED POTENTIAL ENERGY AND A VARIABLE FLOW RESISTOR

RELATED APPLICATIONS

This application is a divisional patent application of U.S. patent application Ser. No. 13/041,296, filed on Mar. 4, 2011, which claims the benefit of and priority to U.S. Provisional Patent Application No. 61/310,601, filed on Mar. 4, 2010, which applications are incorporated herein by reference in their entireties.

TECHNICAL FIELD

The present disclosure relates to systems and methods for infusing drugs, and more particularly to systems and methods for infusing drugs at a constant flow rate throughout the infusion.

BACKGROUND

Infusions remain ubiquitous in healthcare, spanning a wide range of conditions, substances, access sites and venues. Despite advances in oral and other drug delivery modes (e.g. transdermal, inhaled) many critical therapies still require intravenous (IV) infusion. It is estimated that one million infusions are administered per day in the United States. Over 90% of hospitalized patients receive an IV infusion.

Infused substances may include drugs (e.g. antibiotics, chemotherapy, pain medications, local anesthetics, vasoactive agents, biologics), fluids (e.g. crystalloids, colloids, parenteral nutrition) and blood products (e.g. red cells, plasma, platelets). These substances are typically infused as a single bolus volume (a few milliliters to several liters) over a limited time period (minutes to hours) or a continuous infusion delivered a fixed or titrated rate (typical range 0.05 ml to 5 ml per minute) over a more prolonged time period (hours to days).

Infusions may be administered through a variety of routes, most commonly intravenous but also intraarterial, subcutaneous, intrapleural, intraarticular, epidural and intrathecal. A wide variety of catheters and implantable ports are available to facilitate infusions in through these various routes.

Although infusions have traditionally been administered in hospital settings, an increasing number of patients are receiving infusions in ambulatory infusion centers and at home. Because these latter settings have fewer and less-skilled clinical personnel, only certain infusions are deemed to be safe to administer in such non-hospital settings including intravenous antibiotics, certain chemotherapeutic agents, local anesthetics for postoperative pain control and certain narcotic pain medications.

Current healthcare infusions technologies typically involve the use of gravity, active displacement electric pumps or non-electric disposable elastomeric pumps. However, there maybe certain disadvantages with these approaches. Gravity driven infusions have low capital and disposable costs but require careful monitoring by a nurse, can be inaccurate, can limit patient mobility, and have no patient safety features. Electric pumps are accurate (±3%) and have built in safety features of debatable efficacy but can be expensive, bulky, susceptible to human factors and have limited mobility. Disposable elastomeric pumps are convenient and fairly inexpensive, but oftentimes lack patient safety features, can be very inaccurate (±15-40%) and thus have little or no role in hospital based infusions.

The landmark 1999 Institute of Medicine report, "To Err is Human", attributed 40-100,000 deaths per year in the U.S. to medical errors. Medication errors, 40% of which are serious, life-threatening or fatal, are the most common medical error and cost the health care system billions of dollars per year. Intravenous medication errors are the most common medication error and over 35% of these are related to infusion pumps. Studies have shown that despite progressively feature-laden "smart pumps," human factors, software and hardware issues continue to contribute to serious errors. The FDA's MAUDE Adverse Event reporting system contain numerous examples of serious injury and death related to infusion pump errors, both electric and disposable. In the past four years over 600,000 electric infusion pumps from the two leading manufacturers have been recalled over major software and hardware problems leading patient injury and death.

The current state of healthcare infusions can thus be summarized as follows. Although hospital, ambulatory center and home infusions remain central to modern healthcare, infusion pump errors remain a major problem and contribute significantly to the large human and economic burden of medical errors. Electric infusion pumps have become expensive, high maintenance, complex technologic devices with well intentioned "smart" features of unclear benefit. Disposable infusion pumps have many attractive features but most are still inaccurate and may lack basic patient safety features making them inappropriate for most intravenous infusions.

SUMMARY

In one aspect of the present disclosure, there is provided an infusion device that includes a plunger situated within a vessel so as to define a chamber within which a volume of fluid can be accommodated between a downstream surface of the plunger and the vessel. The infusion device further includes an outflow path through which the fluid in the chamber can be dispensed upon displacement of the plunger by a force acting thereon. A variable flow resistor is situated within the outflow path and being configured to vary resistance to fluid flow from the chamber, so as to maintain a substantially constant fluid flow rate from the vessel as the force acting on the plunger decreases.

In another aspect of the present disclosure, there is provided a method for delivering fluid that includes a step of providing within a chamber, defined between downstream surface of a plunger and a vessel within the plunger is situated, a volume of fluid to be delivered. Next, a force may be caused to act on the plunger to displace the plunger within the vessel, such that the fluid is dispensed from the chamber. As the fluid is dispensed, the resistance to flow maybe varied within a path through which the fluid is being dispensed from the chamber as the force on the plunger decreases, so as to maintain a substantially constant rate of dispensing.

In yet another aspect of the present disclosure, there is provided an infusion device including a plunger situated within a vessel so as to define a chamber within which a volume of fluid can be accommodated between a downstream surface of the plunger and the vessel. The device may also include an outflow path through which the fluid in the chamber can be dispensed upon displacement of the plunger by a force acting thereon. A variable flow resistor may be situated downstream of the outflow path and being configured to receive the fluid from the chamber, the resistor configured to maintain a substantially constant pressure therein, so that such pressure can act to deliver the fluid from the resistor at a substantially constant rate, as the force acting on the plunger decreases.

In a further aspect of the present disclosure, there is provided a method for delivering fluid that includes providing within a chamber, defined by a downstream surface of a plunger and a vessel in which the plunger is situated, a volume of fluid to be dispensed. Next, a force may be caused to act on the plunger to displace the plunger within the vessel, such that the fluid is dispensed from the chamber. Subsequently, the fluid dispensed from the chamber may be received in an environment designed to maintain a substantially constant pressure that can act to dispense the fluid from the environment. In the next step, the fluid may be dispensed from the environment while maintaining a substantially constant difference in pressure upstream and downstream of the aperture, thereby providing a constant flow rate of fluid to a patient as the force on the plunger declines.

In another aspect of the present disclosure, there is provided a pressure regulator that includes an inlet cavity and a housing. A plunger may be situated within the housing to define an outflow cavity between a downstream surface of the plunger and the housing. The device also includes a channel for fluid communication between the inlet cavity and the outflow cavity, so as to maintain equilibrium of balance of forces acting on each side of the plunger. The fluid can be dispensed from the outflow cavity from an outlet in the housing.

BRIEF DESCRIPTION OF DRAWINGS

FIG. 1 is a cross sectional depiction of a vessel of the infusion device of the present disclosure.

FIGS. 2A-2E show horizontal cross sections (at a level noted by the dotted line in FIG. 2A) of several embodiments of the vessel of the infusion device of the present disclosure.

FIGS. 3A-3C show the plunger system 23 within the empty vessel in three different positions, when the fluid chamber is full (FIG. 3A), partially empty (FIG. 3B) and completely empty (FIG. 3C).

FIGS. 4A-4E show various embodiments of a mechanism for driving the plunger.

FIGS. 5A-5D show various embodiments of the infusion device of the present invention in various states.

FIGS. 6A-6D show an embodiment of a variable flow resistor of the present disclosure.

FIGS. 11A-11C show an embodiment of a variable flow resistor of the present disclosure.

FIG. 13 shows an infusion system with an array of infusion devices of the present disclosure.

DETAILED DESCRIPTION

Figure 3A:
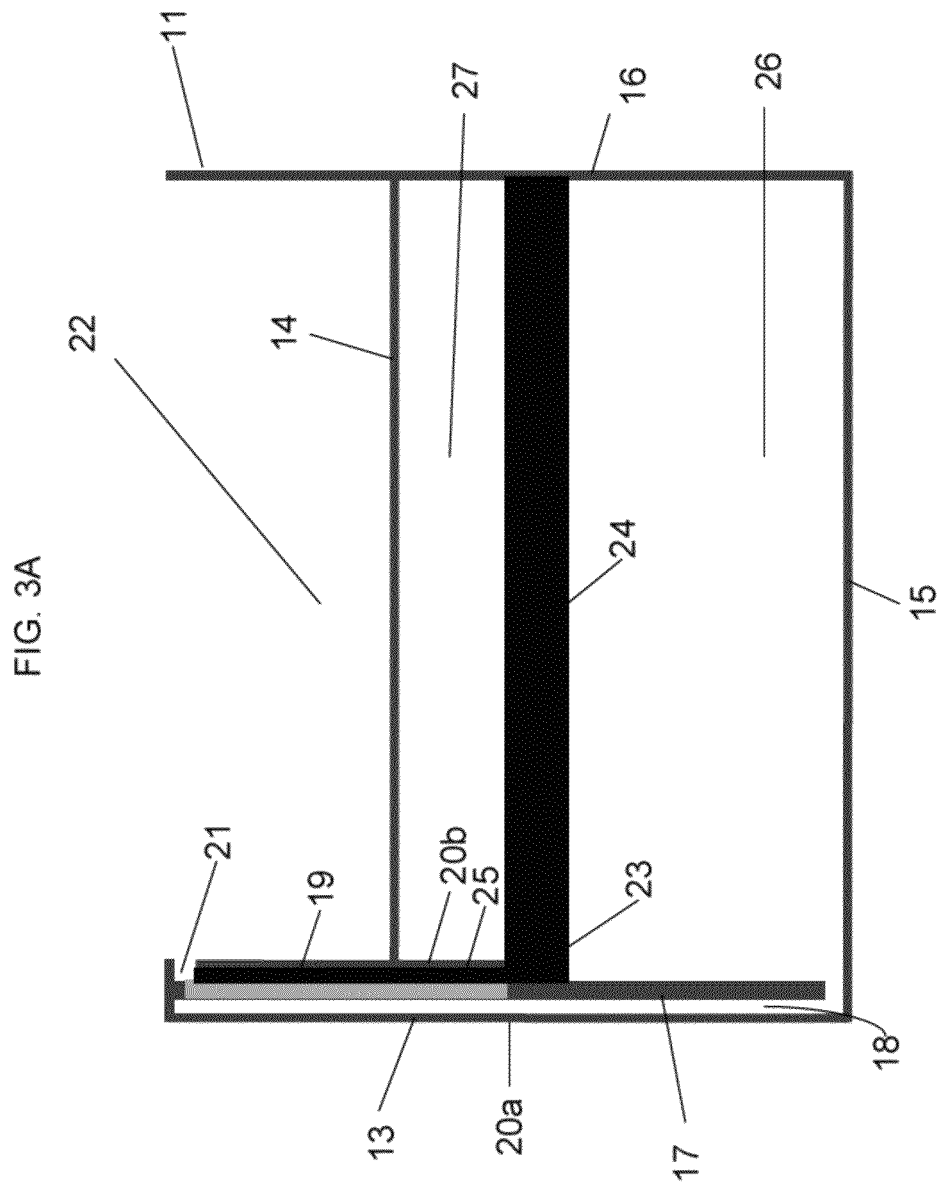

FIG. 1 presents an embodiment of a device 10 of the present invention for infusion of drugs and/or fluids into a patient. The infused fluid may include a wide range of drugs, fluid feedings, biological therapies, other substances and combinations thereof. The infused fluid may be administered intravenously, enterally, intraarterially, directly into a cardiac chamber, subcutaneously, intramuscularly, through another parenteral route or into a body cavity, including, but not limited to, the peritoneal space, pleural space, pericardial space, joint space, epidural space, spinal space or cerebral ventricles.

The device 10, in an embodiment, may include a vessel 11 with one or more chambers. Of course, the vessel 11 may be of any shape or size, as desired. The vessel 11 may be made from a durable, disposable, or recyclable material. In an embodiment, the vessel 11 may have a hard shell exterior to safely enclose the pressurized fluid, gases or other substances contained therein. For example, the vessel 11 may be made of plastic (e.g. polycarbonate, polypropylene), metal, glass or any other lightweight material to facilitate portability.

In an embodiment, vessel 11 of device 10 may include a main chamber 12. Geometrically, the main chamber 12 may be a right prism such as a cuboid, cylinder or any other three-dimensional structure with fixed cross-sectional shape across a given height. As such, the main chamber 12 may have a top wall 14, bottom wall 15 and one or more lateral walls 16. The lateral wall(s) 16 of the vessel 11 may, in an embodiment, extend past the top wall 14 of the main chamber 12 to form a bay 22. The bay 22 may be provided to hold a control module, tubing, connectors, adaptors and other accessories to enhance the functionality of the infusion device 10. In addition, by extending the lateral wall 16 to match the height of outflow path 13, the device 10 may assume a substantial practical, ergonomic shape.

As noted, vessel 11 of device 10 may include an outflow path 13 in fluid communication with the chamber 12. In an embodiment, the outflow path 13 may be situated along an edge of the vessel 11. Outflow path 13 may be provided with a width substantially narrower than width of the main chamber 12. The outflow path 13 may, in an embodiment, project for a distance beyond the top wall 14 of the main chamber 12. Although illustrated as part of vessel 11, it should be noted that the outflow path 13 may be spaced away from the main chamber 12 and be fluidly connected to the main chamber 12 by, for example, a tube.

With reference now to FIGS. 2A-2E, the cross section of the main chamber 12, as noted, may be of any shape including, but not limited to rectangular, circular, ellipsoid or other more complex shape. FIGS. 2B-2E show a cross section of several embodiments of the vessel with differing shapes for the main chamber 12 at the level of the dotted line A in FIG. 2A. By the way of a non-limiting example, the vessel 11 may be provided with a rectangular shape (FIG. 2B), circular shape (FIG. 2C), or curved, elongated rectangular shape (FIG. 2E), or the vessel 11 may bullet shaped (FIG. 2D). In certain embodiments, the depth of the outflow path 13 can be less than the depth of the main chamber 12, as shown in FIGS. 2B and 2C, or equal to the depth of the main chamber 12, as shown in FIGS. 2d and 2E.

Figure 3B:
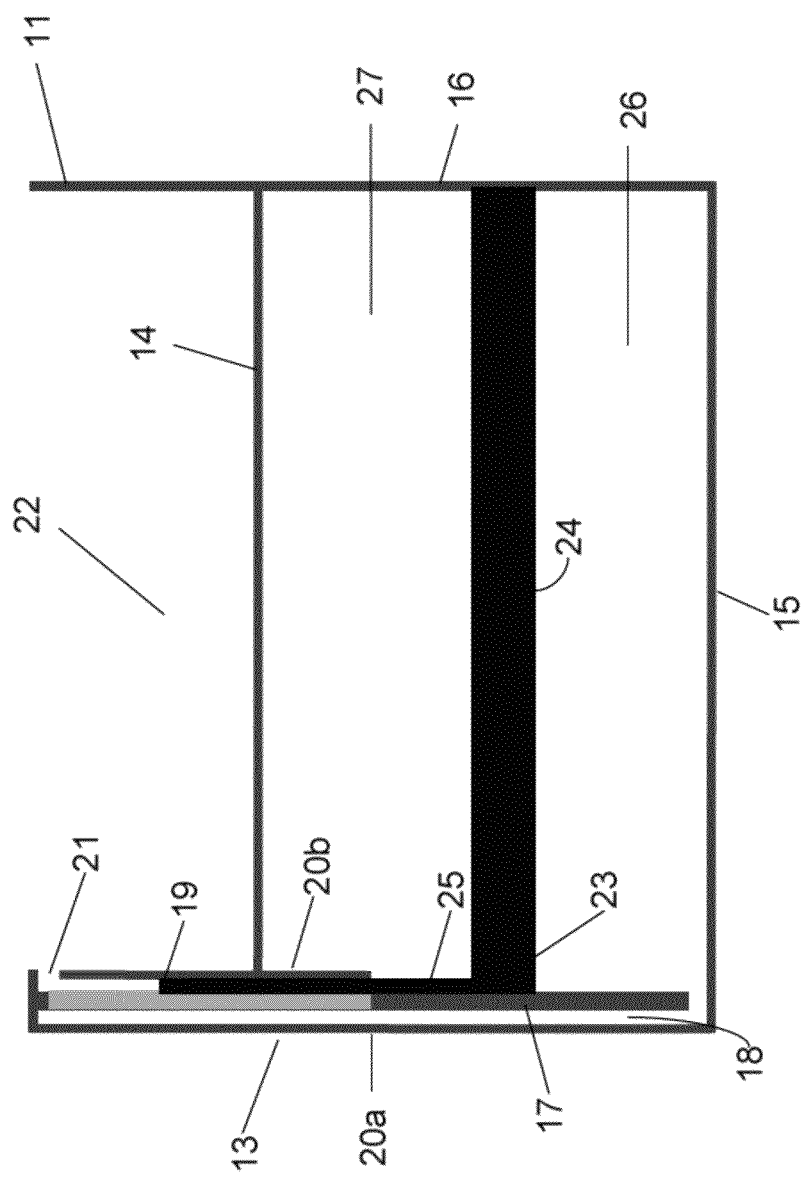

Now with reference to FIGS. 3A-3C, in an embodiment of the device 10 of the present disclosure, a plunger system 23 may reside within the vessel 11. The plunger system 23 may partition the chamber 12 into a fluid chamber 26 for storing a volume of fluid and a pressure chamber 27 for housing a mechanism for displacing the plunger system 23 within the vessel 11. FIG. 3A shows the plunger system 23 at a point in the main chamber 12 where the plunger system 23 may be positioned when the fluid chamber 26 is substantially full. FIG. 3B shows the plunger system 23 at a point in the main chamber 12 where the plunger system 23 may be positioned when the fluid chamber 26 is partially empty. FIG. 3C shows the plunger system 23 at a point in the main chamber 12 where the plunger system 23 may be positioned when the fluid chamber 26 is substantially empty.

The plunger system 23, in an embodiment, may include a main plunger 24. The main plunger 24 may reside within the main chamber 12 and serve as a movable wall, similar to a plunger in a standard syringe. The plunger 23 defines the fluid chamber between its downstream surface and the vessel. The main plunger 24 may move axially within the main chamber 12, changing the relative volumes of the fluid chamber 26 and the pressure chamber 27 respectively. In addition, as it moves within the main chamber 12, the main plunger 24 may provide a substantially tight seal with the walls of the main chamber 12 to prevent leakage of gas or fluid between the fluid chamber 26 and the pressure chamber 27. To that end, the main plunger 24 may be of an appropriate shape and structure to allow the main plunger 23 to provide such a seal, while being able to slide freely within the main chamber 12. In an embodiment, the main plunger 24 may form a substantially snug fit with the main chamber 12 of the vessel 11 to provide coefficient of friction between the main plunger 24 and the walls of the main chamber 12 that may be sufficiently low to so as to permit the main plunger 24 to move it within the main chamber 12. In an embodiment, the main plunger 24 may be made of a pliable material such as silicone, latex or other rubber material. In another embodiment, main plunger 24 may be made of a rigid material such as plastic or metal with an outer gasket made of a pliable material such as rubber or silicone. In an embodiment, the main plunger 24 may include a gasket to further facilitate isolating the fluid chamber 26 and the pressure chamber 27 from one another. The gasket may be sufficiently lubricated to allow the main plunger 24 to move freely within the main chamber 12. The main chamber 12 may, in an embodiment, include one or more guide mechanisms to stabilize the main plunger 24, as the main plunger traverses the main chamber 12. Such a guide, in one embodiment, can be a post through the center of the main chamber 12 or ridges and/or grooves in the inner aspect of the lateral wall(s) of the main chamber 12.

To displace the main plunger 24, the pressure chamber 27 may, in an embodiment, house a driving mechanism configured to store potential energy and to release potential energy to displace the plunger system 23 within the vessel 11. Such driving mechanism by its nature may store sufficient amount of the potential energy to displace the main plunger 24 sufficiently to infuse the fluid into the patient without the need for any outside power source, pump or gravity. The potential energy, in one embodiment, may impart a force on the main plunger 24 sufficient to administer the fluid from the fluid chamber 26 through the outflow path 13 to the patient at a desired flow rate. To provide the driving mechanism with sufficient potential energy, the fluid chamber 26 can be filled with fluid to expand the fluid chamber 26 and drive the main plunger 24 towards the pressure chamber 27. In that way, the driving mechanism may be compressed, causing the driving mechanism to store the necessary potential energy that can be released for the subsequent infusion.

Figure 4A:
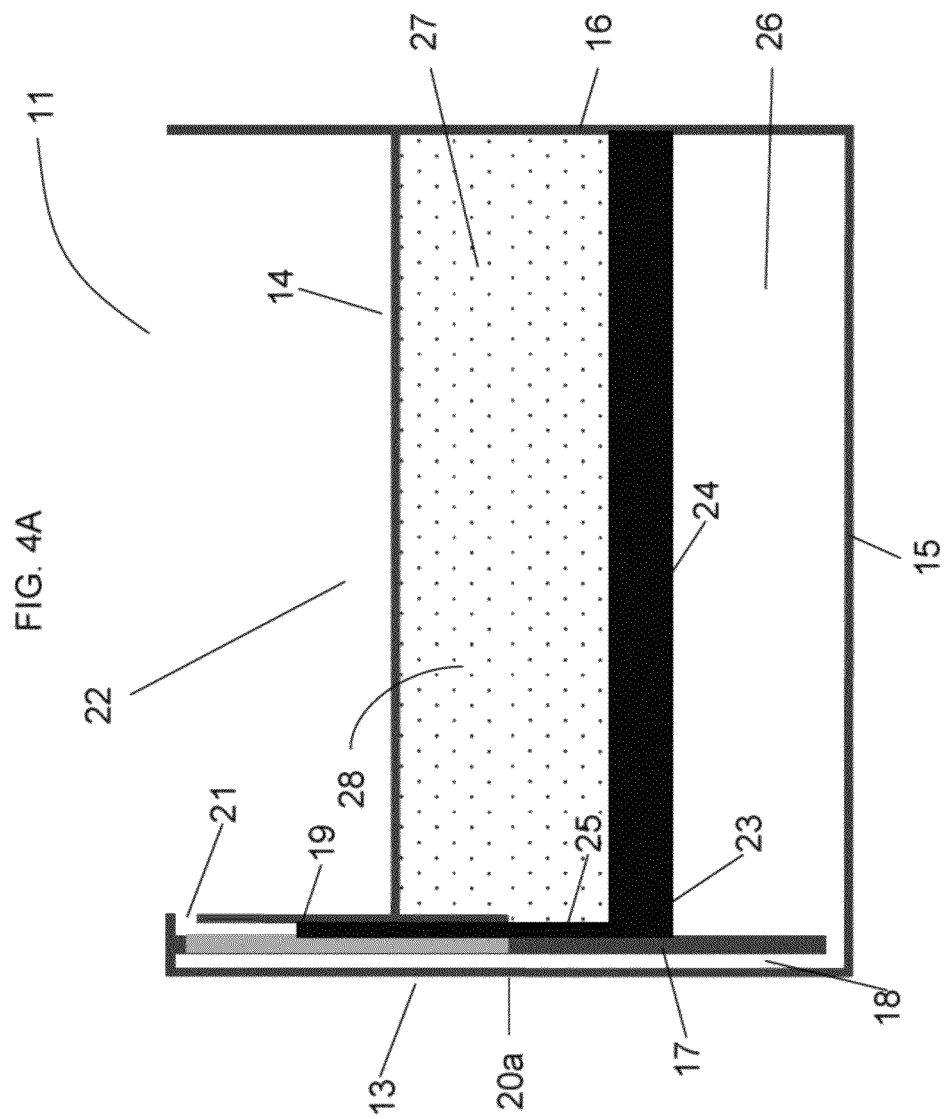

The driving mechanism may, in an embodiment, be in the form of a compressible gas 28, such as shown in FIG. 4A. To withstand the force which compressed gas 28 imparts on its walls, the vessel 11 may, in an embodiment, be made of a sufficiently strong material such as plastic or metal. In addition, the seals between the plunger system 22 and the inner walls of the vessel 11 need to be sufficiently tight enough so that the compressed gas 28 may remain within the pressure chamber 27 and not leak into the fluid chamber 26 or the outflow path 13. In an embodiment, the gas 28 can be any medical grade, non-flammable gas including but not limited to air, carbon dioxide, nitrogen or helium. Additionally, the gas 28 may be capable of being sufficiently compressed so that, when allowed to expand, the gas 28 can generate adequate force on the plunger system 23 to drive it into fluid chamber 26 to infuse the fluid in the fluid chamber 26 into the patient.

The amount of gas 28 sufficient to achieve the desired initial driving pressure on the main plunger 24 can be determined using Boyle's Law, assuming that the gas 28 is operating as an ideal gas:

$$m_g = \frac{P_0 V_0 MW_g}{RT(CR-1)}$$

Where $m_g$ is the mass of the gas 28 in the gas vessel 29, $P_0$ is the initial vessel pressure, $V_0$ is the initial volume in the fluid chamber 26 to be infused, $MW_g$ is the molecular weight of the gas 28, R is the ideal gas constant, CR is the compression ratio of the gas 28 at the beginning of infusion and T is the absolute temperature.

In one embodiment, as depicted in FIG. 4A, the gas 28 can simply fill the space within pressure chamber 27. In another embodiment, as shown in FIG. 4B, the gas 28 may reside within an impermeable, elastic gas vessel 29 disposed within the pressure chamber 27. Having the gas 28 situated within such fully enclosed gas vessel 29 may allow the gas 28 to expand and contract, without the risk of leakage of the gas 28 outside the vessel 11 or into the fluid chamber 26. This may permit higher pressures to be generated within the pressure chamber 27. It may also facilitate manufacture and assembly of the devices of the present disclosure. In an embodiment, the gas vessel 29 can be filled and sealed at atmospheric pressure and then squeezed into the vessel 11 with an external mechanical force, thus eliminating the need for a high pressure gas port on the vessel 11. In an embodiment shown in FIG. 4D, the gas vessel 29 can be bound to the plunger system 23 on top of the main plunger 24, so the combined entity can later be placed into the vessel 11 as a single piece.

Figure 4C:
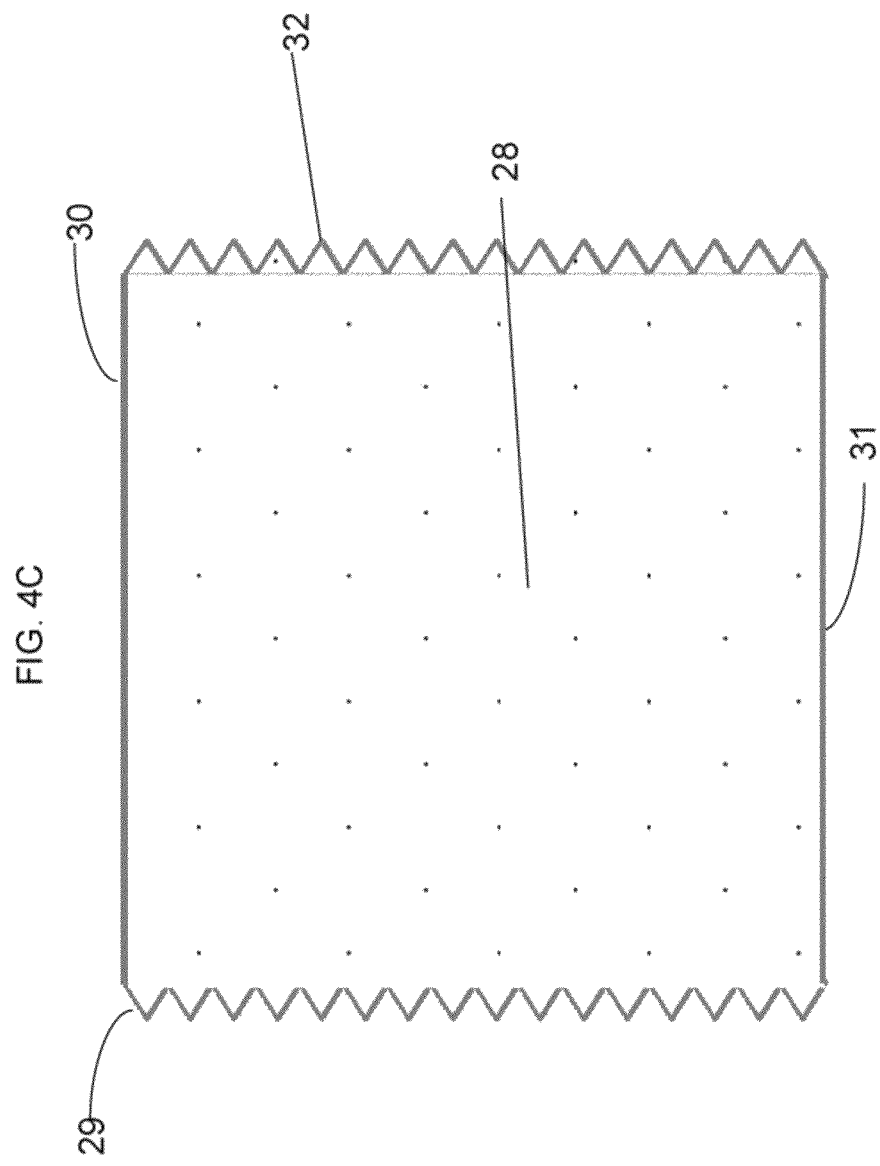

As shown in FIG. 4C, in its neutral state (i.e. non-compressed), with the outside the vessel 11 at atmospheric pressure, the gas vessel 29 may be provided with a shape that roughly matches that of the main chamber 12, namely a top wall 30, a bottom wall 31 and one or more lateral walls 32. In this neutral state, the height of the gas vessel 29 may be greater than that of main chamber 12 because the gas vessel 29 may remain pressurized throughout the duration of the infusion. In an embodiment, the cross-sectional shape of the gas vessel 29 may be the same as the main chamber 12, but with a slightly smaller area to allow is to expand freely within the main chamber 12. The gas vessel 29 can be made from a non-compliant, non-permeable, flexible material such as plastic (polyurethane, polypropylene, PTFE, PBAX, etc.) with an accordion or bellows-like structure which limits expansion and contraction to the axial dimension of the vessel. The top wall 30 and bottom wall 31 can be reinforced with a rigid material such as plastic, glass or metal to further force the expansion and contraction of the vessel to a single, axial dimension. Although similar functionality can be achieved using an elastic or semi-elastic material for the gas vessel 29, the tendency for the lateral wall(s) 32 to expand outward makes manufacture and assembly more cumbersome.

In another embodiment, shown in FIG. 4E, pressure chamber 27 can store its potential energy in a mechanical device, such as one or more springs 33 situated between the top wall 15 of the main chamber 12 and the main plunger. One or more springs may be used to provide a desired force to drive the plunger system 23 and the selection of which may be in accordance with Hooke's law.

In an embodiment, the pressure chamber 27 may include one or more vents in communication with the atmosphere to provide an inlet for air as the pressure chamber 27 expands. Venting the pressure chamber 27 may prevent a vacuum from being generated in the pressure chamber 27, the presence of which may hinder the expansion of the pressure chamber 27. Venting the pressure chamber 27 may also help to avoid overheating of the mechanism for driving the plunger system 23. Venting may further assist in removing any air trapped between the gas vessel 29 and the inner walls of the main chamber 12.

In reference to FIGS. 5A-5D, in an embodiment, the device of the present disclosure may include one or more inlet ports 34, outlet port 35, integrated tubing 36, terminal connector 37 and adapters 38. These ports may include caps to seal the opening when necessary, or valves to permit fluid or gas to move in the proscribed direction. The inlet ports 34, outlet ports 34, terminal connector 37 and adapters 38 may possess specific connector mechanisms such as luer-lock, screw-on, bayonet or other "quick connect" style mechanisms to aid in the operation of the device 10 and/or the dispensing of the infusion fluid 40. For instance, the inlet ports 34 may be used to fill the fluid chamber 26 or fill the gas vessel 29. The outlet port 35 may allow the fluid and air to leave the vessel during deairing and fluid to leave during the infusion. The integrated tubing 36 may be of an appropriate length to reach the patient and in its preferred embodiment is coiled so that it more ergonomic. The terminal connector 37 may connect the device to a patient's catheter 39 or port, either directly, or using a matching adapter 38 previously connected to the catheter or port.

Figure 5B:
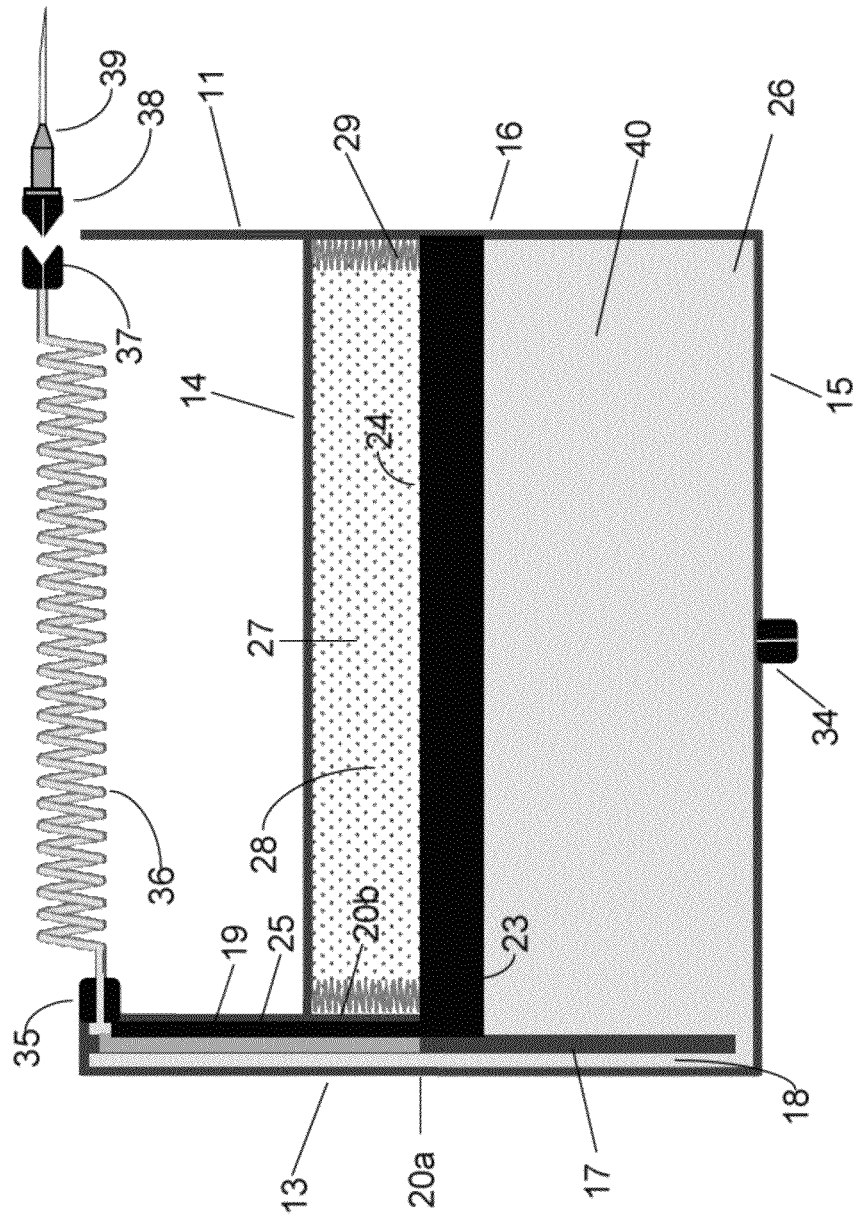
Figure 5C:
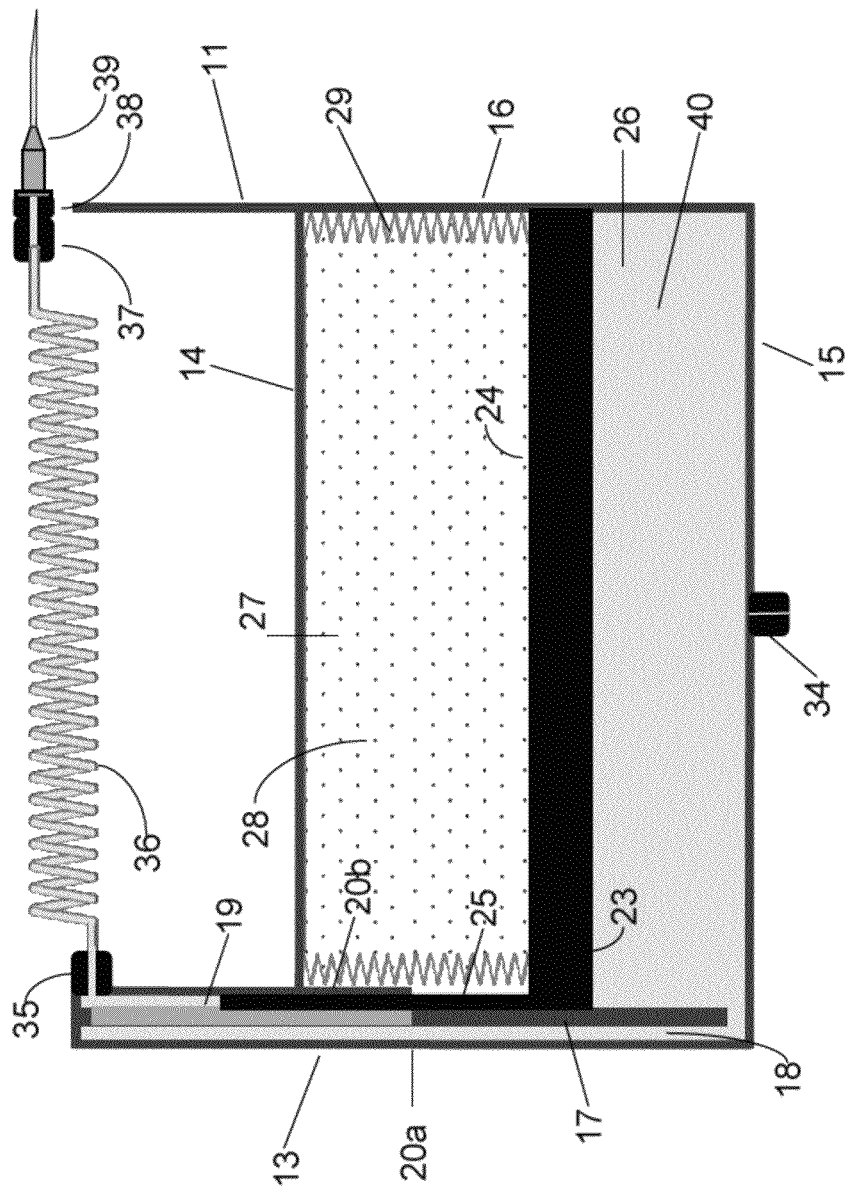

In reference to FIG. 5A, in an embodiment, the fully assembled and charged, but empty infusion device 10 is shown ready to be filled. Vessel 11 is shown with a partially charged pressure chamber 27 containing the gas vessel 29 with the gas 28. The gas 28 is fully expanded in the main chamber 12, such that the volume of the fluid chamber 26 is substantially zero. As shown, the outflow path 13 and integrated tubing 36 may be full of air and the terminal connector 37 is not yet attached to the catheter 39. FIG. 5B shows the same device filled with infusion fluid 40 and de-aired, ready to begin the infusion. In particular, vessel 11 is shown with the gas 8 in the pressure chamber 27 compressed. The fluid chamber 26, outflow path 13 and integrated tubing 36, on the other hand, are shown substantially full of fluid and devoid of air. In the embodiment shown in FIG. 5B, the main plunger 24 is at its highest position, abutting the edge of the inner wall 20. This position of the main plunger 24 corresponds with a maximum volume of the fluid chamber 26, a minimum volume of the pressure chamber 27 and a maximum pressure in all chambers. FIGS. 5C and 5D show the device after 50% and 100% of the infusion of the infusion fluid 40 has been completed.

As the infusion fluid 40 is dispensed from the fluid chamber 26 by the displacement of the main plunger 24, the infusion fluid may enter the outflow path 13. In an embodiment, as illustrated in FIGS. 3A-3C and 5A-5D, the outflow path 13 may be formed between walls 20a and 20b of the vessel 11. An outflow septum 17 may be disposed within the outflow path 13. In an embodiment, the outflow septum 17 may be fully integrated into the structure of the vessel 11. In an embodiment, the outflow septum 17 can be manufactured separate from the vessel and inserted into a slotted channel in the vessel during assembly. This may permit a given size vessel to be married to one of several outflow septa 17, each with its own resistance properties, to achieve the desired flow rate for that particular infusion device.

The outflow path 13 may be divided by an outflow septum 17 into two parallel outflow channels: an outer outflow channel 18 and inner outflow channel 19. The outflow channel 18 may be defined by the space between the outflow septum 17 and the wall 20a. The outflow septum 17 can extend from the distal tip of the outflow path 13 down towards, but just short of the bottom wall 15 of the vessel 11, providing a flow path from the main chamber 12 into the outer outflow channel 18. Outer outflow channel 18 may terminate at the distal tip of the outflow path 13 as a dead end. The inner outflow channel 19 may be defined by the space between the outflow septum 17 and the wall 20b. The wall 20b may extend for a distance into the main chamber 12 from its top wall 14, forming a portion of the wall of the inner outflow channel 19. Inner outflow channel 19 may terminate at the distal tip of the outflow path 13 at an outflow orifice 21. A section of the outflow septum 17 may be permeable, permitting flow from the outer outflow channel 18 into the inner outflow channel 19.

The infusion device 10 may further include, in an embodiment, a plunger extension 25. The plunger extension 25 may be a reed-like projection that extends orthogonally from one edge of the main plunger 24. As with the main plunger 24, the plunger extension 25 may be made wholly of a pliable material such as rubber or silicone or of a rigid material such as plastic or metal with an outer layer of rubber or silicone to form a gasket. The plunger extension 25 may reside within the inner outflow channel 19 of the outflow path 13 and may form a tight seal within inner outflow channel 19 to prevent leakage of fluid or gas into the fluid chamber 26 or pressure chamber 27. The length of the plunger extension 25 may be such that when the fluid chamber 26 is empty and the main plunger 24 is up against the bottom wall 15 of the main chamber, as shown in FIG. 3C, the plunger extension 25 may remain engaged within the inner outflow channel 19, with enough overlap to maintain a seal. When the fluid chamber 26 is filled with fluid, the plunger extension 25 may extend high up into the inner outflow channel 19. In an embodiment, the plunger extension 25 may be short of the end of the channel so it does not occlude the outflow orifice 21, as illustrated in FIG. 3A. The inner wall 20 of the main chamber 12 may be sized such that the plunger system is prevented from rising up to occlude the outflow orifice 21. As the main plunger 24 moves towards the bottom wall 15 of the main chamber 12, it may pull the plunger extension 25 along with it. As the plunger extension 25 moves proximally within the inner outflow channel 19, it may increase the height of the outflow channel 19. The plunger extension 25 may also slide along the outflow septum 17, increasing the area of the septum which communicates with both the inner and outer outflow channels 18 and 19.

In an embodiment, the infusion device 10 of the present invention may include a variable flow resistor disposed within the outflow path 13. The variable flow resistor may assist in maintaining a constant flow rate during the infusion with a high degree of accuracy. Conventional disposable infusion pumps typically attempt to deliver a given flow rate by incorporating a fixed flow resistor in the infusion circuit, typically a segment of narrow caliber tubing interposed between the pump and the patient. The driving force for these pumps, typically provided by a recoil of an elastomeric membrane or spring, however, is not constant, but may vary throughout the duration of the infusion and may decline toward the end of the infusion. Since the resistance to flow is constant, the flow rate from such pumps may vary as the driving force varies. For instance, it has been shown that instantaneous flow rate deviations in some disposable infusion pumps as high as ±40%. By providing a variable flow resistor in the outflow path 13, the infusion fluid may be infused into the patient at substantially constant flow rate for the duration of the infusion, even as the driving force varies.

With reference to FIGS. 6A-6D, in an embodiment, a variable flow resistor 60 of the device of the present disclosure may be formed by the interaction of the permeable portion of the outflow septum 17 and the plunger extension 25. In an embodiment, outflow septum 17 may have a permeable portion defined by permeable area 41 and permeable area 42. By providing the septum 17 with such a permeable area, as the plunger extension slides along the outflow septum 17 away from the outflow orifice 21, an increasing portion of the permeable section of the outflow septum 17 may be exposed, allowing the flow between the inner outflow channels 18 and the outer outflow channel 19 to occur at a higher rate to accommodate any decrease in the force exerted by the plunger on the fluid in the fluid chamber 26.

The permeable section of the outflow septum 17 may, in an embodiment, be divided into two areas: the initial permeable area 41 and the adjustable permeable area 42. At the beginning of the infusion, shown in FIG. 6A, the plunger extension 25 may be at its highest point. To that end, the plunger extension 25 may substantially cover the adjustable permeable area 42, when the plunger extension 25 may be at its highest point. The initial flow may proceed through the initial permeable area 41 which is situated on the outflow septum 17 distal to the highest point of the plunger extension 25, directly opposite the outflow orifice 21. Permeable area 41 can be made of the same material and can be contiguous with the adjustable permeable area 42, as shown. Alternatively, the initial permeable area can be separate and made of a different material. The resistance to flow of this initial permeable area 41 can determine the initial flow rate.

As the infusion proceeds, as shown in FIG. 6B, the plunger extension 25 may move away from the outlet 26 within the inner outflow channel 19, exposing an increasing portion of the adjustable permeable area 42. According to Darcy's law, which governs the flow of fluid through a homogeneous permeable material, the resistance to flow of the adjustable permeable area 42 is inversely proportional to the exposed area. As such, when the force on the infusion fluid in the fluid chamber 26 declines as the infusion progresses, an increased permeable area is needed to lower resistance in order to be able to maintain a substantially constant flow rate of the infusion fluid from the infusion device. When the infusion is substantially completed, as depicted in FIG. 6C, the plunger extension 25 may be at its lowest point on the outflow septum 17, all of the adjustable permeable area 42 may be exposed and the resistance to flow may be at a minimum.

The outflow septum 17 may be made of a rigid impermeable material, similar to the vessel 11 such as plastic or metal. In an embodiment depicted in FIG. 6D, the permeable areas 41 and 42 can include a permeable material of a given shape, embedded in a cut-out in the wall of the outflow septum 17. The material can be any porous material 43 such as plastic, metal, ceramic or fiber with an appropriate permeability index to achieve the desired resistance to flow for a given embodiment of the device. In another embodiment, the permeable areas 41 and 42 can be created by creating a pattern of pores through the outflow septum 17. The initial permeable area 41, can in fact be a single pore of the appropriate diameter to provide the appropriate initial resistance to flow. The adjustable permeable area 42, can have a grid 44 of micropores of a fixed or variable size spread over a given area at a given density. The density of micropores can be fixed or variable. In another embodiment, the permeable areas 41 and 42 can be created by starting with an outflow septum 17 made entirely from the porous material 43 or 44 and applying an impermeable mask with a cutout of the shapes of the permeable areas 41 and 42 to each side of the outflow septum.

The variable flow resistor 60 may track the decline in the force acting on the plunger system 23 as the infusion progresses and may enable a decrease in the resistance to flow of the infusion flow in the outflow path 13 to maintain a constant flow. The variable flow resistor may do that by increasing the height of the exposed portion of the adjustable permeable area 42 of the variable flow resistor 28, thereby decreasing the resistance in a predictable fashion. The relationship between the resistance and the exposed height can be derived from the two laws governing the gas and fluid in the device—Boyle's Law and Pouseille's Law. Once this relationship is determined, the shape of the permeable areas 41 and 42 can be determined using Darcy's Law to establish the relationship between the width and height of the area as shown in FIG. 6B.

Boyle's Law governs the relationship between the pressure and volume of the gas 28 in the pressure chamber 27. Gas 28 may be assumed to be an ideal gas and according to Boyle's law, the product of the pressure and volume of the gas is a constant. Since the fluid is assumed to be non-compressible, the pressure of the gas may be the same as the pressure of the entire vessel under static conditions. Assuming laminar flow, Pouseille's Law governs the relationship between the driving pressure on the fluid, the flow resistance and the flow rate. At a constant flow rate, the ratio of the pressure and resistance to flow may be constant.

Figure 7A:
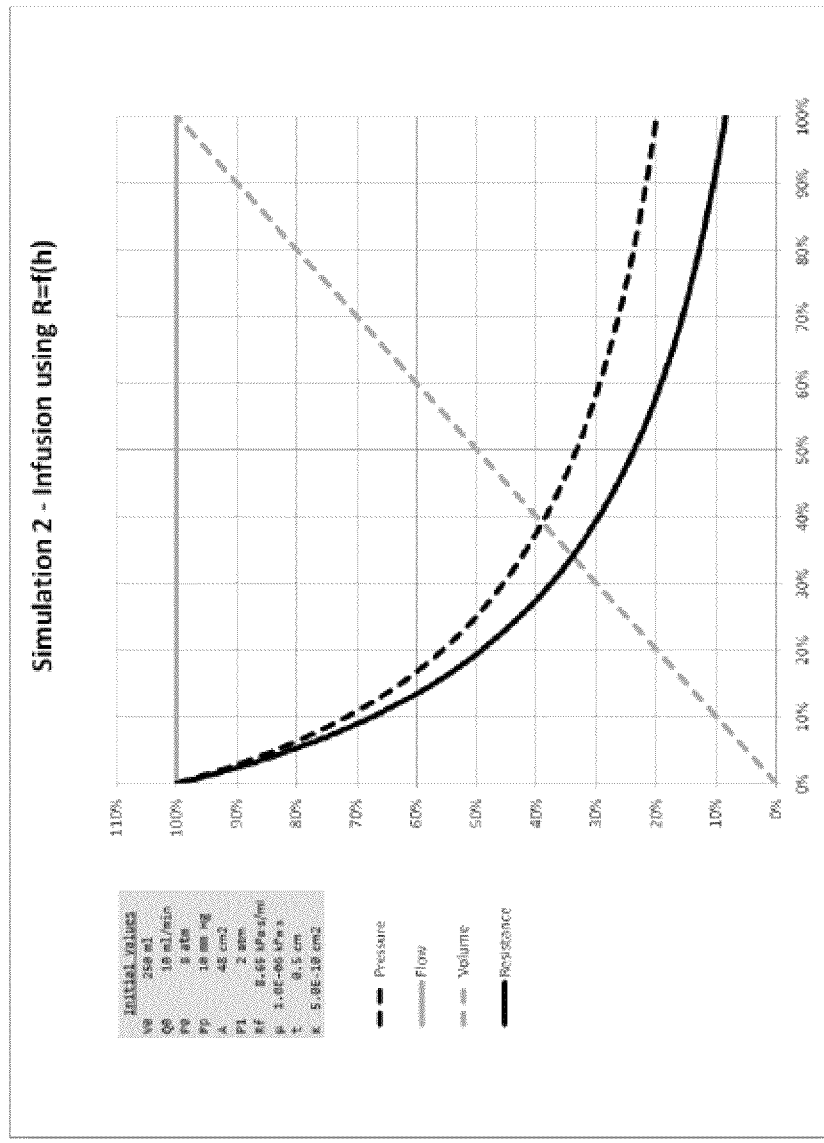
FIGS. 7A-7B show results of a simulation of an infusion using an embodiment of a variable flow resistor of the present disclosure.

Using these two laws, the relationship between the exposed height, h, of the adjustable permeable area 42 of the variable flow resistor and the total resistance R along can be determined to be $$R(h) = \frac{P_0 V_0}{Q_0(V_0 + (P_0 - P_1)Ah)} - \frac{P_p}{Q_0}$$

Where $P_0$ and $P_1$ are the initial and final vessel pressures respectively, $V_0$ is the initial volume in the fluid chamber 26 to be infused, A is the cross-sectional area of the main chamber 12 and therefore also of the fluid chamber 26 and pressure chamber 27, Pp is the pressure at the site of infusion in the patient (e.g. venous pressure), $Q_0$ is the initial and therefore the target flow rate. In numerical simulations of the device using up to 10,000 iterations across a wide variety of initial conditions as well as vessel size and shape, varying the total resistance according to this resistance function can result in a constant flow rate within a tolerance of <0.001%. FIG. 7A shows the results of a typical simulation. The resistance falls steadily as the infusion progresses and the pressure chamber is decompressed resulting in a constant flow.

The total resistance to flow over the entire fluid path can be expressed as several separate resistors. One is the total fixed resistance of the fluid path including the outflow channels 18 and 19, the outlet port 35, integrated tubing 36, terminal connector 37, adapters 38 and patient catheter 39. The variable flow resistor may be in series with the total fixed resistance. The variable flow resistor may have two components connected in parallel, an initial resistance corresponding to the initial permeable area 41 and a variable component which corresponds to the exposed portion of the adjustable permeable area 42.

In the embodiment shown in FIGS. 6A-6C, the permeable areas 41 and 42 may be parts of the outflow septum 17 filled with a homogenous porous material or a pattern of micropores. The initial permeable area 41 is shown as a narrow rectangle but can be of any shape that fits in the upper portion of the outlet septum 17. Its area is such that it generates the precise initial resistance to generate the initial resistance of the device. The area can be determined to be $$a_0 = \frac{\mu t Q_0}{\kappa(P_0 - (P_p + Q_0 R_f))}$$

Where $\mu$ is the fluid viscosity, t is the thickness of the outflow septum 17 and $\kappa$ is the permeability of the adjustable permeable area 42.

The adjustable permeable area 42 is shown in FIGS. 6A-6C to be a trapezoid but the shape required to achieve the resistance function above is more complex and depends on initial conditions and properties of the vessel. If the permeability of the area is assumed to be homogenous across the adjustable permeable area 42 and through the thickness of the outflow septum 17, Darcy's Law can be used to determine the precise shape of the area which will generate the above resistance function and maintain a constant flow rate throughout the duration of the infusion. The shape can be expressed by the relationship between the width of the adjustable permeable area 42 at a given exposed height h of the area as follows.

$$w(h) = \frac{\mu t P_0 V_0 Q_0 A(P_0 - P_1)}{\kappa(P_0 V_0 - (P_p + Q_0 R_f)(V_0 + A(P_0 - P_1)h))^2}$$

Figure 7B:
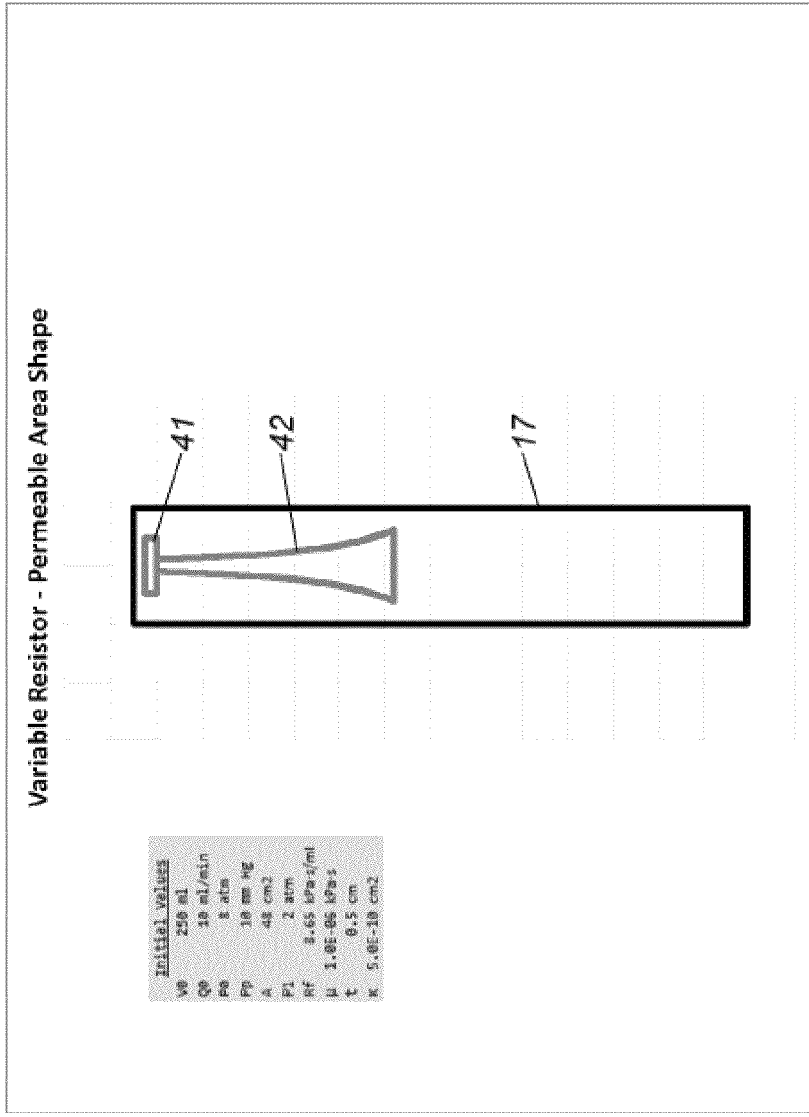

In a number of simulations of the device using up to 10,000 iterations across a wide variety of initial conditions, the above function generates a declining resistance which results in a constant flow within a tolerance of <0.001%. FIG. 7B shows the shape of the permeable area 42 derived from the above shape function using a set of initial conditions shown.

In an embodiment in which the pressure chamber 27 uses a spring instead of gas, similar resistance and shape functions can be derived. In this case, Hooke's Law governs the property of the spring which is assumed to functioning within its linear range where the force is proportional to spring displacement. As a result, the resistance function is linear $$R(h) = \left(\frac{P_0 - P_p}{Q_0}\right) - \frac{A(P_0 - P_1)h}{V_0 Q_0}$$

The area of the fixed permeable area 41 is the same as for the gas version $$a_0 = \frac{\mu t Q_0}{\kappa(P_0 - (P)_p + Q_0 R_f))}$$

The shape of the adjustable permeable area 42 in this embodiment is $$w(h) = \frac{\mu t A V_0 Q_0 (P_0 - P_1)}{\kappa(V_0(P_0 - P_p - Q_0 R_f) - A(P_0 - P_1)h)^2}$$

Figure 8A:
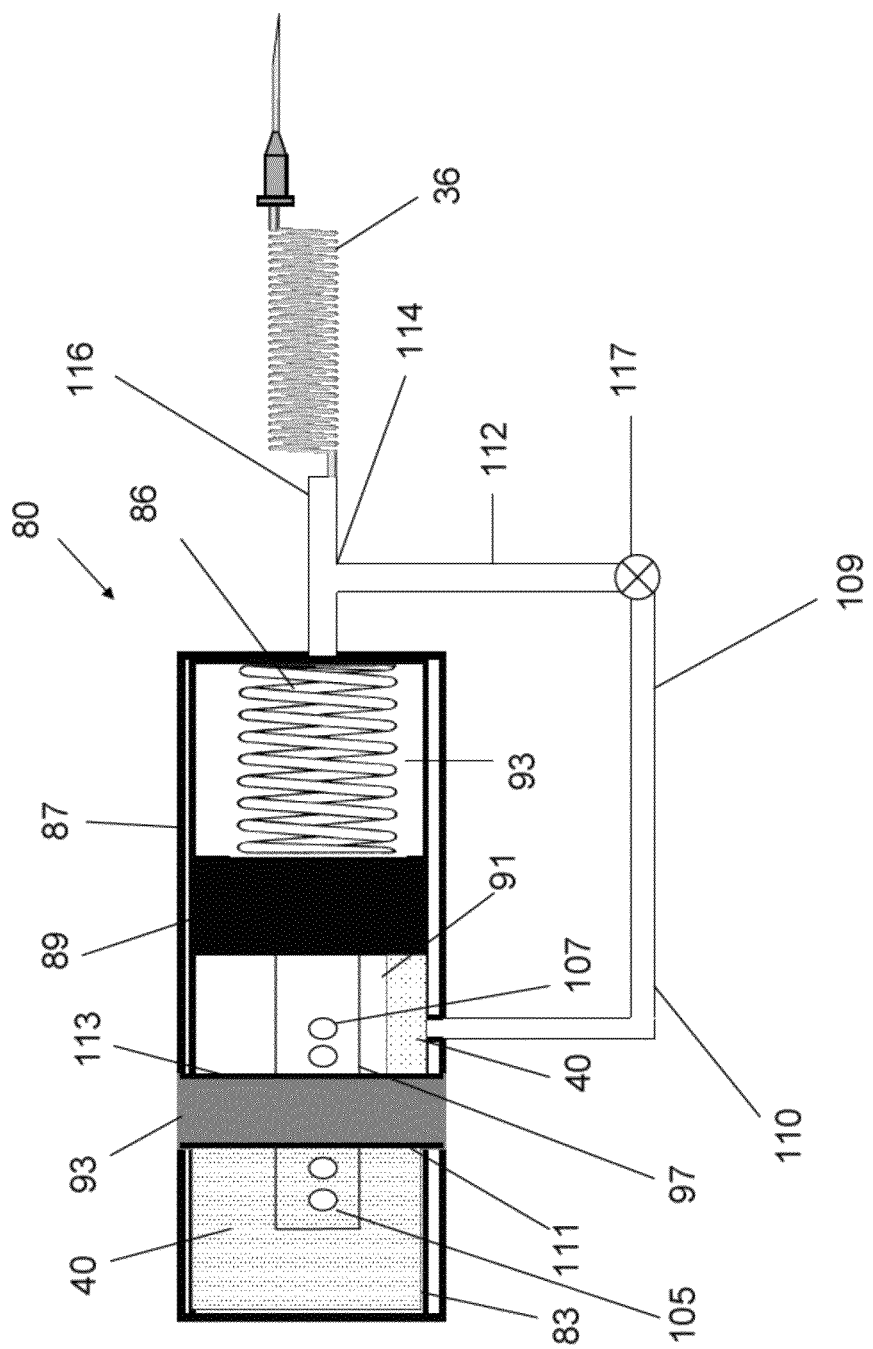
FIGS. 8A-8C show an embodiment of a variable flow resistor of the present disclosure.
Figure 8B:
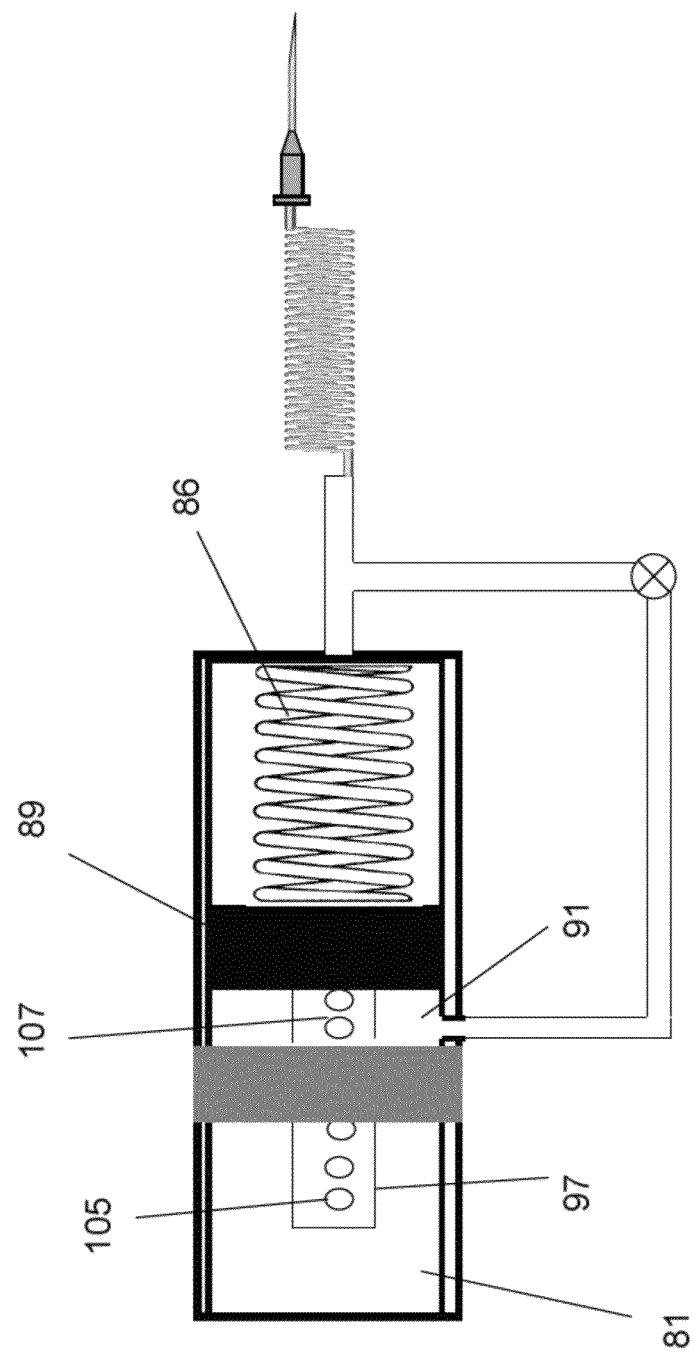
Figure 8C:
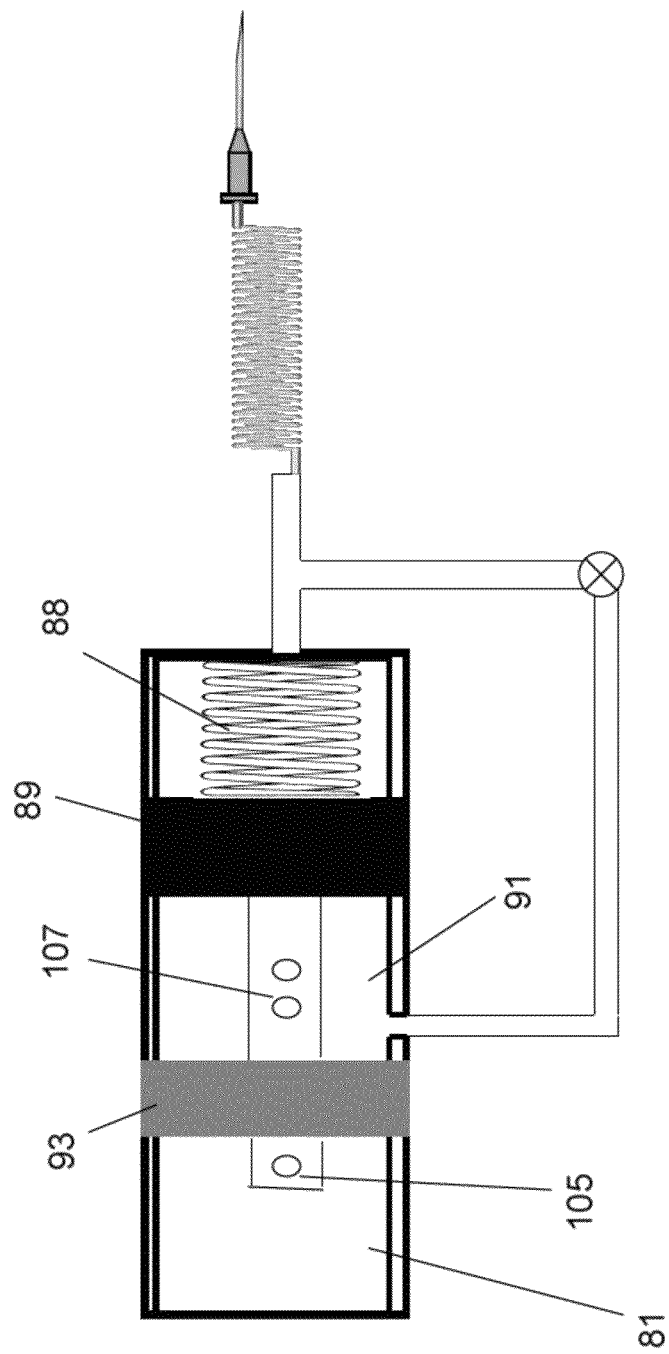

In another embodiment a mechanical variable flow resistor, such as shown in FIGS. 8A-8C, is provided in the outflow path 13. In such an embodiment, the outflow path may be a simple path, unlike the embodiment of the outflow path 13 described above in connection with the passive variable flow resistor 60. To maintain a constant flow rate of the infusion fluid 40 to the patient, the mechanical variable flow resistor may, in an embodiment, provide an intermediate chamber in the outflow path 13 into which the infusion fluid 40 may be transferred from the fluid chamber 26. The mechanical flow resistor of the present invention may maintain a desired difference in pressure in the intermediate chamber and at the point of infusion to enable infusion of the infusion fluid 40 into the patient at a constant flow rate throughout the duration of the infusion. The mechanical flow resistor of the present invention may be provided with a feedback loop and a mechanism that allows to correct for fluctuations in pressure in the intermediate cavity and pressure at the point of infusion, such that the desired difference in pressure is maintained throughout the duration of infusion. Because the infusion fluid 40 is dispensed from the intermediate cavity through a constant aperture, the infusion fluid 40 may thus be administered to the patient at a constant flow rate throughout the duration of the infusion, even as the force on the plunger system 23 decreases.

With reference now to FIGS. 8A-8C, an embodiment of a mechanical variable flow resistor 80 is shown. The resistor 80 may include an inlet cavity 81 in fluid communication with the fluid chamber 26 of device 10 to allow the infusion fluid 40 to be transferred from the fluid chamber 26 to the inlet cavity 81. The infusion fluid 40, in an embodiment, may be stored in the inlet cavity 81 at a pressure corresponding to the pressure exerted on the infusion fluid 40 by the main plunger 24, less pressure drop in the transfer of the infusion fluid 40.

The mechanical variable flow resistor 80 may further include a housing 87. The housing 87 may include a plunger 89 slidably disposed therein to partition the housing 89 into two compartments: an outflow cavity 91 and a drive cavity 92. The outflow cavity 91 may be configured to receive the infusion fluid 40 from the inlet cavity 81. The drive cavity 92, on the other hand, may be configured to accommodate a driving mechanism 86. Mechanism 86 may be a spring or compressed gas. capable of storing and releasing potential energy, such a spring or a compressed gas, for displacing the plunger 89 within the housing 87.

The housing 87 may, in an embodiment, be positioned in line with the inlet cavity 81, such that a wall 111 of the inlet cavity 81 is adjacent to a wall 113 of the outflow cavity 91. To that end, the outflow cavity 91 may serve as an intermediate chamber into which the infusion fluid may be transferred from the inlet cavity 81. In an embodiment, the infusion fluid 40 may be transferred between the inlet cavity 81 and the outflow cavity 91 through a cannula 97.

Figure 9A:
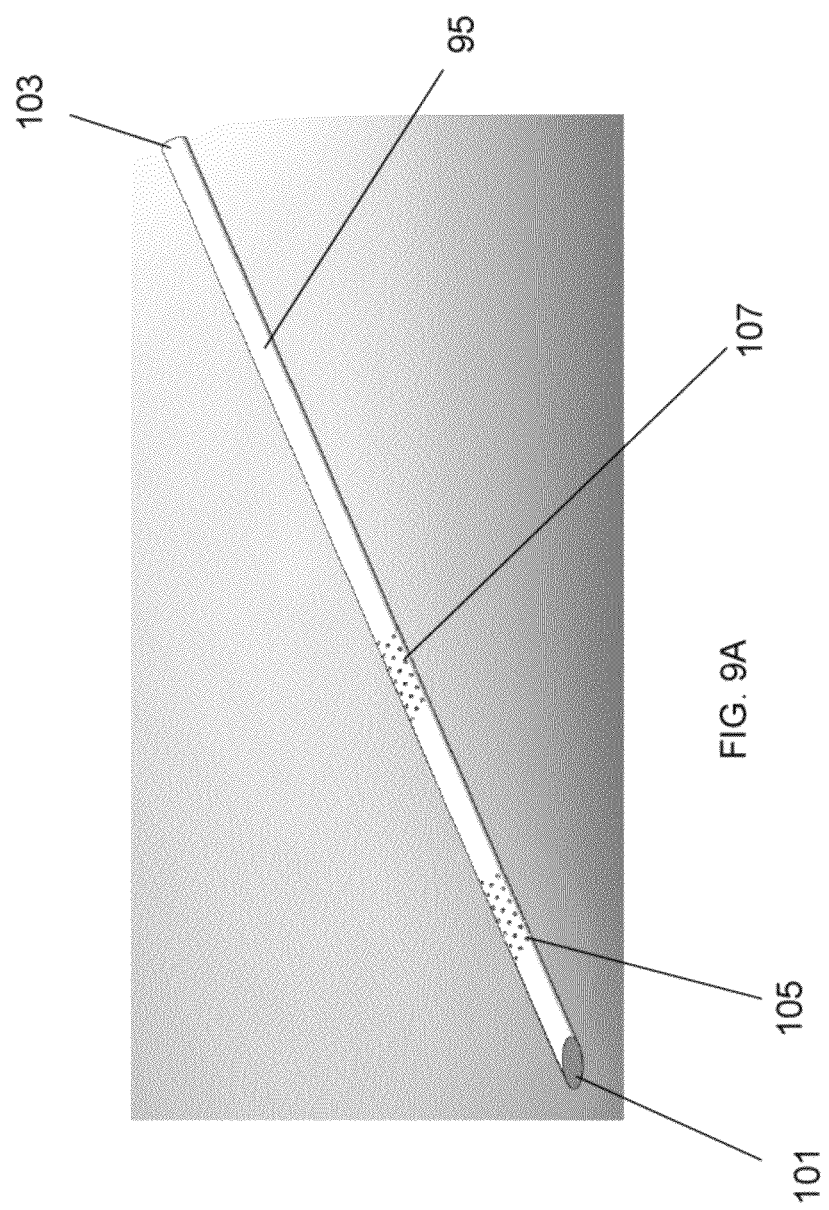
FIGS. 9A-9C show embodiments of a cannula component that may be used in the variable flow resistor of FIGS. 8A-8C.
Figure 9B:
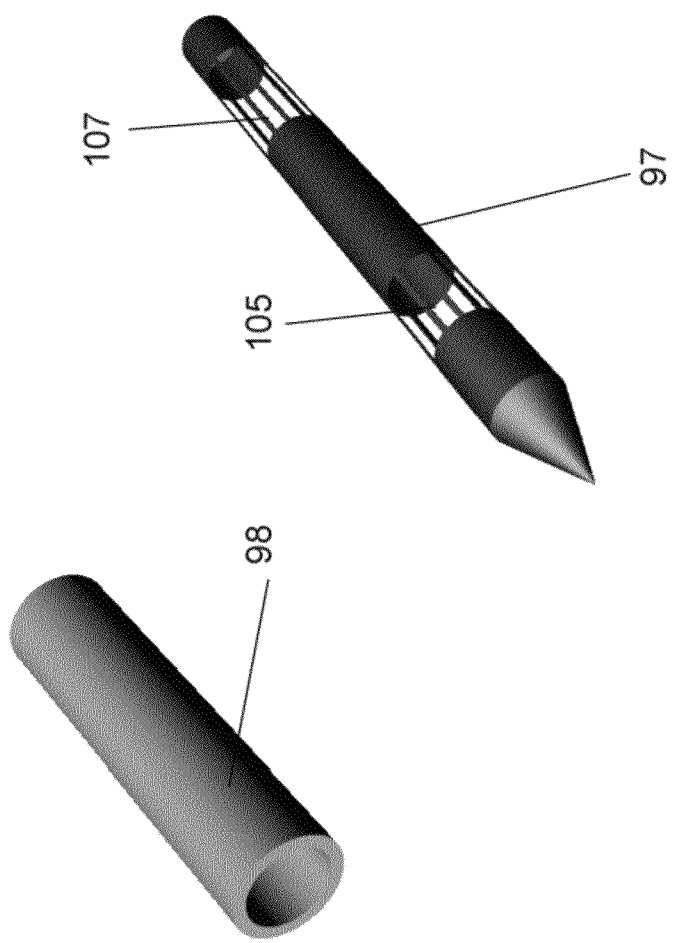
Figure 9C:
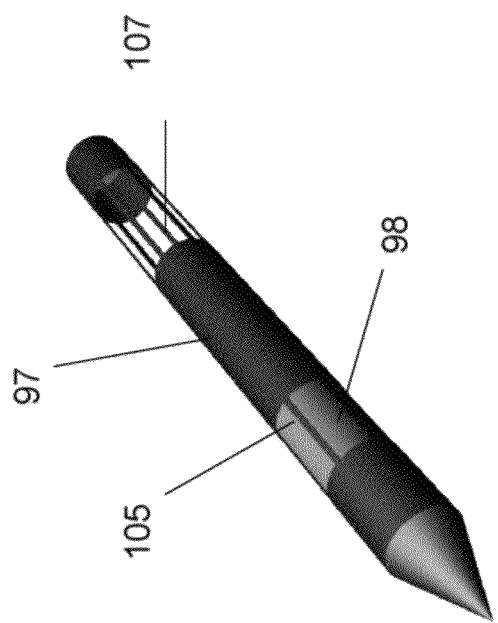

In an embodiment, the cannula 97 may have sealed proximal and distal ends 101 and 103 and a plurality of perforations in a side wall, as illustrated in FIG. 9A. In an embodiment, the plurality of perforations may be grouped into inlet perforations 105 and outlet perforations 107, with inlet perforations 105 spaced apart from the outlet perforations 107. In an embodiment, as shown in FIGS. 9B-9C, a permeable insert 98 may be inserted into the cannula 97. The permeable insert 98 may be aligned with the inlet perforations 105, the outlet perforations 107, or both, to provide a resistance to flow through the cannula 97 in order to regulate pressure drop across the cannula 97.

As shown in FIG. 8A, when the cannula is positioned between the inlet cavity 81 and the outflow cavity 91, at least some of the inlet perforations 105 may be exposed in the inlet cavity 81, while at least some of the outlet perforations 107 may be exposed in the outflow cavity 91, thereby allowing the infusion fluid 40 to flow from the inlet cavity 81 into the outflow cavity 91. In an embodiment, the infusion fluid 40 may not flow through perforations covered by the septum 93. In an embodiment, the infusion fluid 40 may enter the cannula 97 from the inlet cavity 81 through the inlet perforations 105 and exit the cannula 97 into the outflow cavity 91 through the outlet perforations 107.

To control or maintain a substantially constant flow rate, the cannula 97 may be coupled to the plunger 89, such that, the plunger 89 may move the cannula 97 between the housing 87 and the inlet cavity 81 to change the flow rate of the infusion fluid 40 into the outflow cavity 91. As shown in FIG. 8B, moving the cannula 97 into the inlet cavity 81 may expose additional inlet perforations 107, thus allowing the flow rate of the infusion fluid 40 from the inlet cavity 81 into the outflow cavity 91 to increase. On the other hand, as shown in FIG. 8C, moving the cannula 97 out of the inlet cavity 81 may permit the septum 93 to cover additional inlet perforations 105, thus causing the flow rate of the infusion fluid 40 from the inlet cavity 81 into the outflow cavity 91 to decrease.

To ensure that the fluid that the infusion fluid 40 may be transferred between the inlet cavity 81 and the outflow cavity 91 only through the cannula 9, in an embodiment, a septum 93 may be provided between the inlet cavity 81 and the outflow cavity 91. The septum 93 may fluid-tight. The cannula 97 may slide through the septum 93, such the septum 93 may cover some inlet peroration and block flow of the infusion fluid 40 through the covered perforations.

From the outflow cavity 91, the infusion fluid 40 may be dispensed to the patient through a tubing 109, having a valve 117. In an embodiment, the infusion fluid 40 may flow through a first tube 110, through the valve 117, and through a second tube 112 to a t-connector 114. From the t-connector 114, the infusion fluid 40 may flow through a third tube 116 into the integrated tubing 36, which is connected to the patient. In an embodiment, the fourth tube 118 may connect the drive cavity 92 to the integrated through the third tube 116, such that the pressure at the point of infusion of the infusion fluid 40 into a patient may provide backpressure against the plunger 89, as is described in detail below.

In an embodiment, the valve 117 may allow the infusion fluid 40 to be dispensed through a constant, pre-determined aperture. According to Pouseille's law, a constant flow rate may be generated by a constant pressure difference over a constant aperture as follows: $Q=kA(P_d-P_u)$, where Q is flow rate of the infusion fluid 40 into the patient, k is dynamic viscosity of the infusion fluid 40, A is the diameter of aperture of the valve 117 through which the infusion fluid 40 is dispensed, $P_d$ is the pressure downstream of the aperture, and $P_u$ is the pressure upstream of the aperture. That is, the flow rate of the infusion fluid 40 to the patient may be proportional to the difference between the pressure downstream of the valve 117 and the pressure upstream of the valve 117. Once a desired flow rate of the infusion fluid 40 is selected, depending on the particulars of a procedure, the difference between the pressure downstream of the valve 117 and the pressure upstream of the valve 117 needed to maintain the desired flow rate may be determined in accordance with Pouseille's law.

Figure 10:
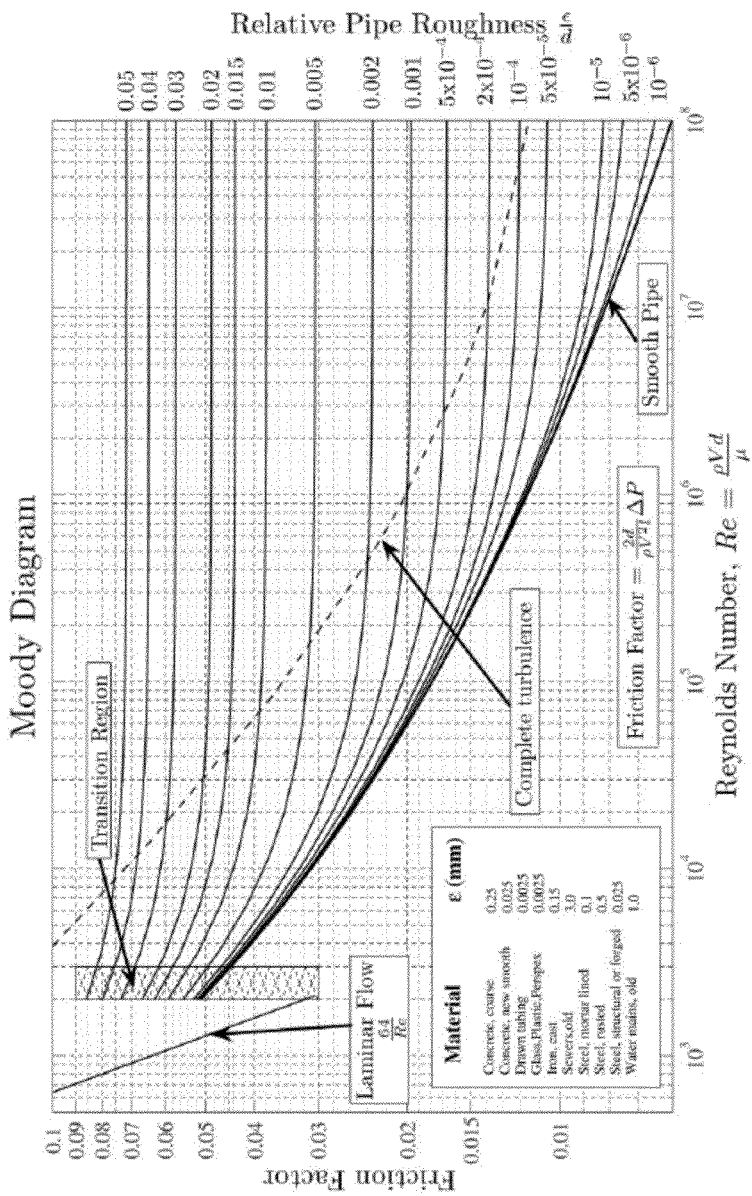
FIG. 10 presents a Moody diagram.

The pressures downstream and upstream of the inlet valve 117 may be determined from the pressure in the outflow chamber 91 and the pressure at the point of infusion, respectively, with accounting for pressure drop. In an embodiment, the pressure downstream of the inlet valve 117 may be substantially equal to the pressure in the outflow chamber 91, $P_1$, while the pressure upstream of the flow valve 117 may be substantially equal to the backpressure acting on the fluid being administered to the patient, which is referred to herein as the patient pressure, $P_2$. The pressure, $P_1$, in the outflow chamber 91 may be dependent on the pressure to the pressure of the infusion fluid 40 in the fluid chamber 26 and design of the cannula 97. In reference to FIG. 8A, the pressure in the inlet chamber, $P_0$, may correspond to the pressure of the infusion fluid 40 in the fluid chamber 26, with a discount for any pressure drop between the fluid chamber 26 and the inlet cavity 81. Moreover, the pressure drop over perforations in the cannula 97 may be calculated from the following Darcy-Weisbach equation and the Moody Diagram presented in FIG. 10:

$$\Delta P = f * \frac{\rho V^2}{2} * \frac{l}{d}$$

where f is the friction factor, ρ is the fluid density, V is the average fluid velocity, l is the thickness of the cannula wall, and d is the perforation diameter. The patient pressure may be determined experimentally or estimated from literature.

In order to dispense the infusion fluid 40 to the patient at a constant flow rate, a substantially constant difference may be maintained between the pressure in the outflow chamber 91 and the patient pressure. The mechanical variable flow resistor 80 of the present disclosure may, in an embodiment, include a feedback loop to allow the mechanical variable flow resistor 80 to maintain a substantially constant difference between the pressure in the outflow chamber 91 and the patient pressure. The mechanical variable flow resistor may be designed such that, when a desired difference between the pressure in the outflow chamber 91 and the patient pressure is maintained, the plunger 89 may be positioned at an equilibrium position within the housing 87. For instance, the equilibrium position may be a position of the plunger when some, but not all, of the inlet perforations 105 in the cannula 97 are located outside the septum 93 in the inlet cavity 81, as illustrated in FIG. 8A.

When the plunger 89 is stationary, the balance of forces acting on the plunger 89 may be defined generally as follows:

$$\pi R^2 P_1 - \pi R^2 P_2 - F_{mech} = 0$$

where R is the outside radius of the plunger 89, $P_1$ is the pressure in the outflow chamber, $P_2$ is the patient pressure, and $F_{mech}$ is the force exerted on the plunger by the mechanism 86. In an embodiment the spring is utilized to drive the plunger 89, $F_{mech}$ exerted by the spring 89 on the plunger 89 may be calculated in accordance with Hooke's law. In another embodiment where compressed air is used to drive the plunger 89, $F_{mech}$ exerted by air on the plunger 89 may be calculated in accordance with Boyle's Law. The forces acting on the plunger that result in the displacement of the plunger to the right, i.e. the displacement of the plunger results in the expansion of the outflow chamber, are defined as positive. The equation above may be re-arranged as follows:

$$(P_1 - P_2) = \Delta P = \frac{F_{mech}}{\pi R^2}$$

Since R, $P_1$, $P_2$ may be estimated or known, a suitable mechanism 86 that may maintain the plunger 89 in the equilibrium position at a desired difference between $P_1$ and $P_2$ may be selected, or vise versa.

In an embodiment, a suitable mechanism 86 may include a spring which can act on the plunger 89 as needed to maintain the plunger 89 in the equilibrium position. The force exerted on the plunger by the spring may be calculated according to Hooke's Law, as follows:

$$F_{spring} = k*(D+x)$$

where $F_{spring}$ is force that the spring may exert on the plunger, k is the spring constant, D is the amount the spring has been pre-compressed, and x is the amount the plunger may move to hold the plunger in the equilibrium position. In an embodiment, the spring is pre-compressed, such that small motions of the spring, such as when the difference between $P_1$ and $P_2$ changes, do not change the spring force.

During the infusion, when a desired difference between $P_1$ and $P_2$ is maintained, the mechanism 86 may hold the plunger 89 substantially stationary in the equilibrium position. If, however, the difference between $P_1$ and $P_2$ decreases, such as, for example, due to the decrease in the force acting on the main plunger 25, the plunger 89 and the cannula 97 may be forced to move from the equilibrium position to the left, i.e., in the direction to expand the drive cavity 92, as shown in FIG. 8B. Such displacement of the cannula 97 may cause additional inlet perforations 105 to be exposed in the inlet fluid cavity 81, thereby allowing the flow rate of the infusion fluid 40 from the inlet cavity 81 into the outflow cavity 91 to increase. The increased flow rate into the outflow cavity 91 may allow $P_1$ to increase, so as to move the plunger 89 back to the equilibrium position. On the other hand, if the difference between $P_1$ and $P_2$ increases, such as, for example, due to the decrease in the patient pressure, the plunger 89 and the cannula 97 may be forced to move from the equilibrium position to the right, i.e., in the direction to compress the drive cavity 92, as shown in FIG. 8C. Such displacement of the cannula 97 may cause additional inlet perforations 105 to be blocked by the septum 93, thereby causing the flow rate of the infusion fluid 40 from the inlet cavity 81 into the outflow cavity 91 to decrease. The decreased flow rate into the outflow cavity 91 may cause $P_1$ to decrease so as to allow the plunger 89 to move back to the equilibrium position. In this manner, the mechanical variable flow resistor 80 of the present disclosure may maintain a substantially constant difference between the pressure in the outflow cavity 91 and the patient pressure.

Figure 11A:
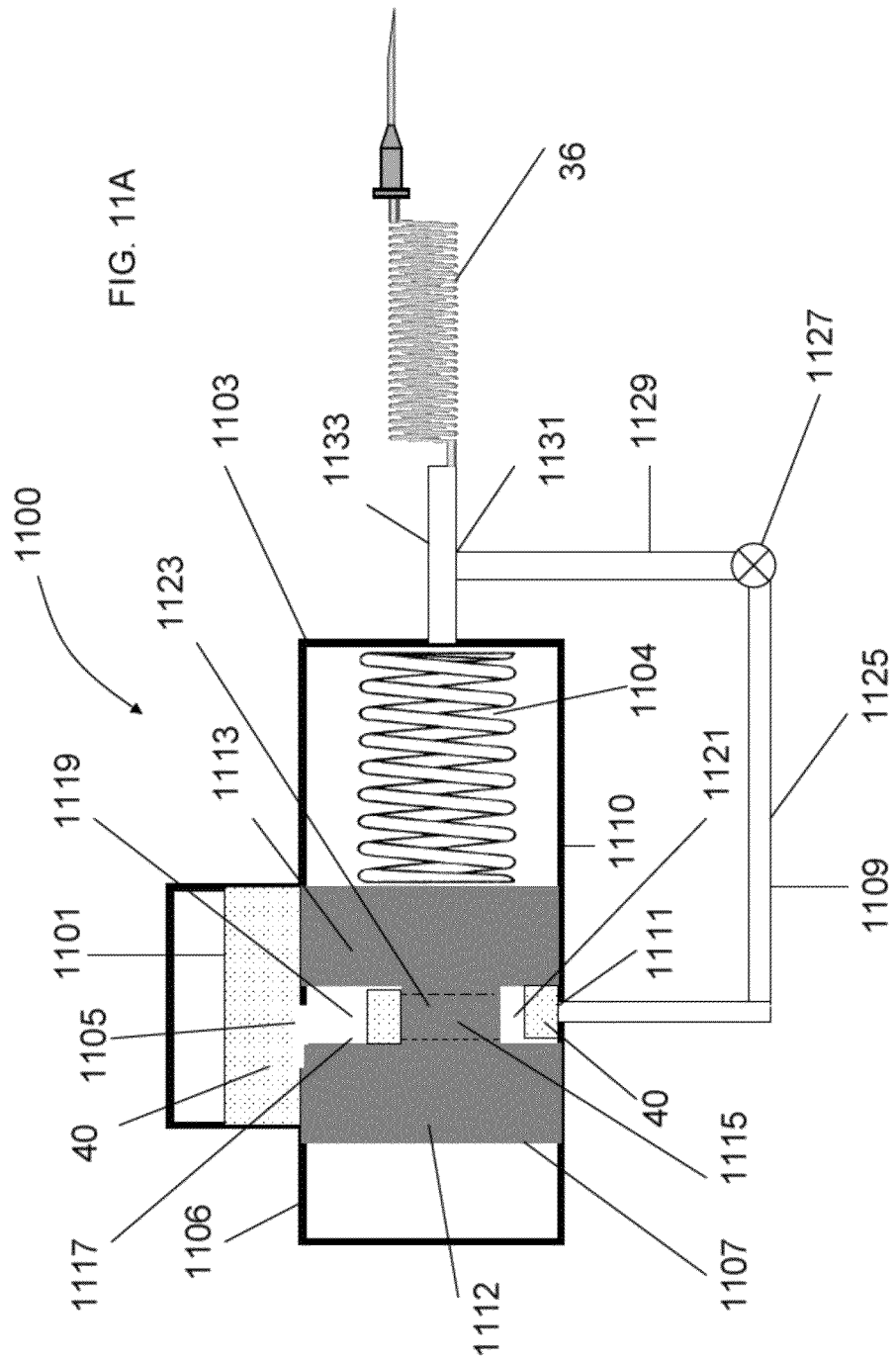

Another embodiment of a mechanical variable flow resistor of the present disclosure is illustrated in FIGS. 11A-11C. In an embodiment, as illustrated 11A, the mechanical variable flow resistor 1100 may include an inlet chamber 1101 in fluid connection with the fluid chamber 26, so as to allow the infusion fluid 40 to be transferred from the fluid chamber 26 to the inlet cavity 1101. The infusion fluid 40 may be pressurized in the inlet cavity 1101 to a pressure corresponding to the pressure exerted on the infusion fluid 40 by the main plunger 24, less pressure drop due to the transfer of the infusion fluid 40.

The mechanical variable flow resistor 1100 may further include a housing 1103. The housing 1103 may be in fluid communication with the inlet cavity 1101 through an inlet opening 1105 in a top wall 1106 of the housing 1103 and with a tubing 1109 through an outlet opening 1111 in a bottom wall 1110 of the housing 1103. A plunger 1107 may be movably disposed within the housing 1103. The housing 1103 may also include a mechanism 1104 capable of storing and releasing potential energy, such a spring or a compressed gas, for displacing the plunger 1107 within the housing 1103. The mechanism 1104 may be disposed in a drive cavity 1108 within the housing 1103.

In an embodiment, the plunger 1107 may be H-shaped, with a first side 1112 and a second side 1113 connected to the first side 1112 by a bridge 1115. The plunger 1107 may define an outflow cavity 1117 between the first side 1112 and the second side 1113. The bridge 1115 may partition the outflow cavity 1117 into a first void 1119 and a second void 1121. The first void 1119 may be in fluid communication with the inlet cavity 1101 through the inlet opening 1105 and the second void 1121 may be in fluid communication with the tubing 1109 through the outlet opening 1112. The first void 1117 and the second void 1121 may be connected by a channel 1123 through the bridge 1115.

As noted above, a pressure acting on the infusion fluid 40 may cause the infusion fluid to flow from the inlet cavity 1103 into the first void 1117. The infusion fluid 40 may then flow through the channel 1123 into the second void 1119 and out of the second void 1123 into the tubing 1109. In an embodiment, the infusion fluid 40 may then flow through a first tube 1125, through a valve 1127, and through a second tube 1129 to a t-connector 1131. From the t-connector 1131, the infusion fluid 40 may flow through a third tube 1133 into the integrated tubing 36. Similarly to the valve 117 described above, the valve 1127 may allow the infusion fluid 40 to be dispensed through a constant, pre-determined aperture. In an embodiment, because the infusion fluid 40 is dispensed to the patient through a constant aperture of the valve 1127, maintaining a substantially constant difference between the pressure downstream of the valve 1127, $P_1$, and the pressure upstream of the valve 1127, $P_2$, for the duration of the infusion may allow the infusion fluid 40 to be infused at a substantially constant flow rate for the duration of the infusion.

When a desired difference in pressure, $P_1-P_2$, can be maintained, the plunger 1107 may be held stationary in an equilibrium position. The equilibrium position may, in an embodiment, refer to a position of the plunger 1107 in which the first side 1111 blocks a portion of the inlet opening 1105. When the difference in pressure decreases, such as, for example, due to the decrease in the force acting on the main plunger 25, the plunger 1107 may be forced to move from the equilibrium position to the left, i.e., in the direction to expand the drive cavity 1108. Such displacement of the plunger 1107 may decrease the blocked portion of the inlet opening 1105, thereby increasing the flow rate of the infusion fluid 40 from the inlet cavity 1101 into the outflow cavity 1117, as shown in FIG. 11B. The increased flow rate into the outflow cavity 1171 may allow $P_1$ to increase, so as to move the plunger 1107 back to the equilibrium position. On the other hand, if the difference between $P_1$ and $P_2$ increases, such as, for example, due to the decrease of the patient pressure, the plunger may be forced to move to the right, i.e., in the direction to compress the drive cavity 1108. Such displacement of the plunger 1107 may increase the blocked portion of the inlet opening 1105, thereby decreasing the flow rate of the infusion fluid 40 from the inlet cavity 1101 into the outflow cavity 1117, as shown in FIG. 11C. The decreased flow rate into the outflow cavity 1117 may cause $P_1$ to decrease so as to allow the plunger 1107 to move back to the equilibrium position. In this manner, the mechanical variable flow resistor 1100 of the present disclosure may maintain a substantially constant difference between the pressure in the outflow cavity 1117 and the patient pressure.

Figure 12A:
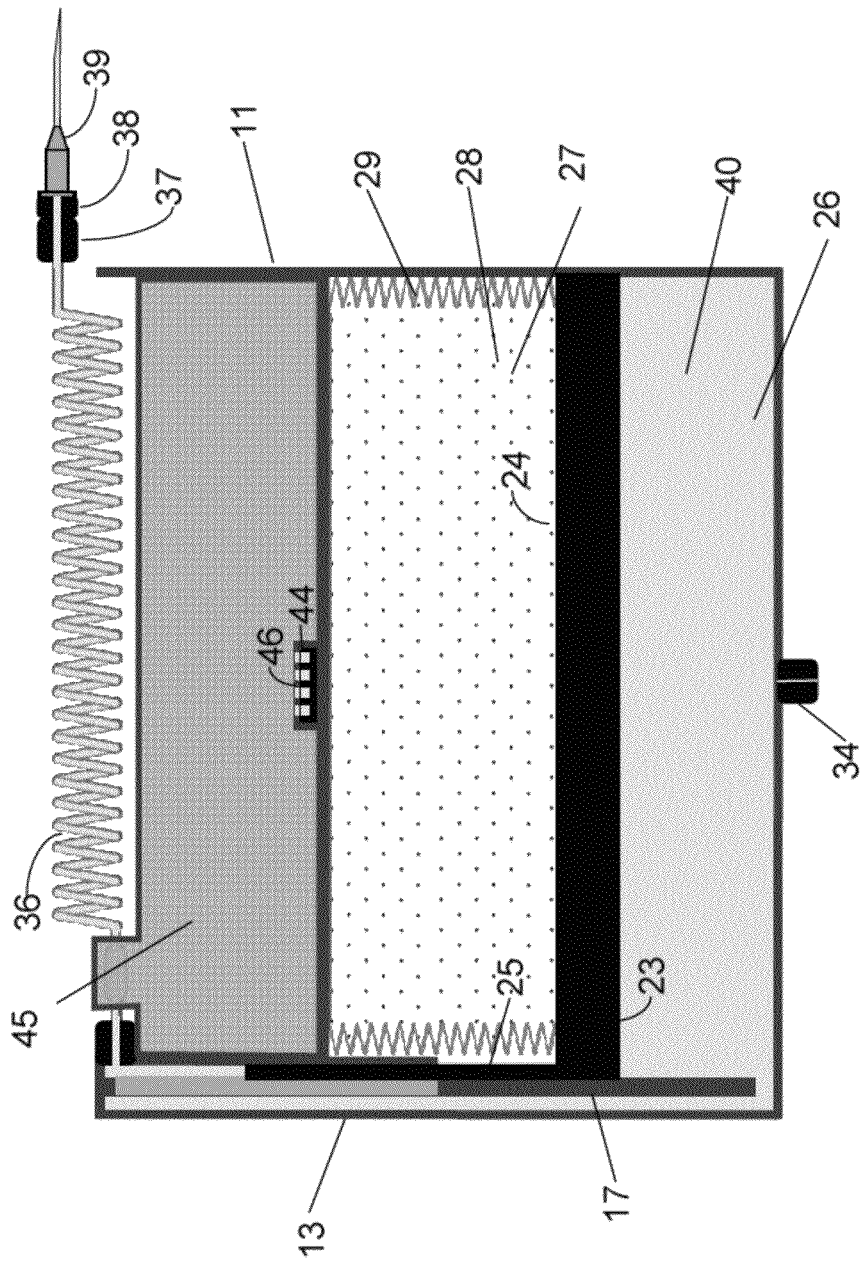
FIGS. 12A-12D show various embodiments of a infusion device of the present disclosure.

In an embodiment shown in FIG. 12A, infusion devices of the present invention may be programmable with an integrated non-volatile memory chip 44 and non-disposable or multi-use disposable electronic control module 45 which attaches to the vessel 11 and communicates with its memory chip 44. In an embodiment, the memory chip 44 may be capable of communicating with various devices though a electronic lead/connector 46 such as SmartCard lead or through a standard USB-type connector. The memory chip 44 can be programmed by a desktop/notebook computer or a handheld device via the above lead/connector 46. The data in the memory chip 44 can be read by a variety of devices with the appropriate matching lead/connector.

Figure 12B:
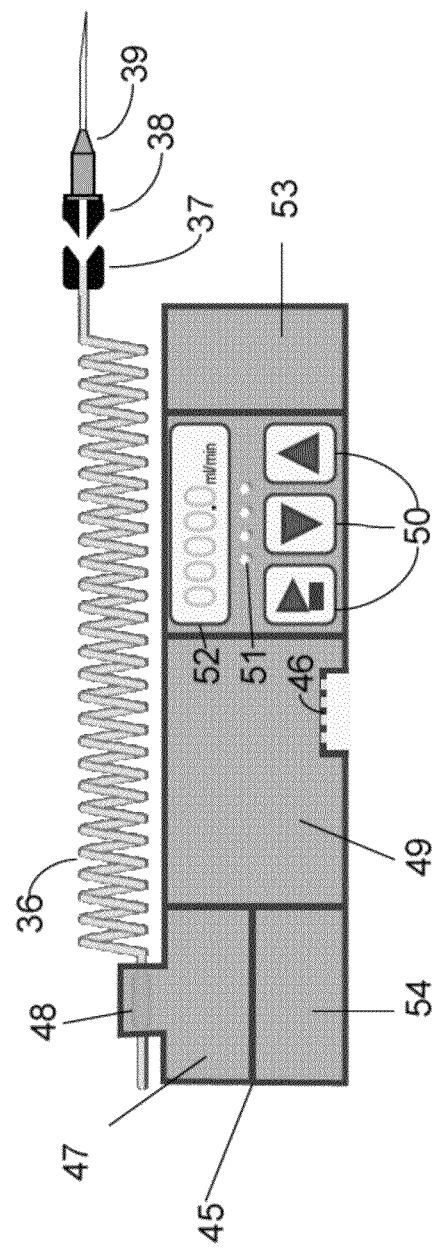

As shown schematically in FIG. 12B, in an embodiment, the electronic control module 45 may include a binary (fully open or fully closed, default closed) flow valve 47, such as a pinch valve which interacts with a specific segment 48 of the integrated tubing 36 and controls the outflow of the substance from the vessel; microprocessor circuitry 49 for operating the binary flow valve 47 and reading patient and infusion data from the disposable vessel's non-volatile memory unit. The electronic control module 45 may also include buttons 50 to control the infusion (e.g. "Run", "Pause", "Up", "Down"); simple visual 51 or audio indicators (e.g. LED's, beeps) and/or a simple electronic display 52 (e.g. LED, LCD) to notify the operator of status of the infusion and simple sensors to detect flow, air, ambient temperature, barometric pressure, etc.

Figure 12C:
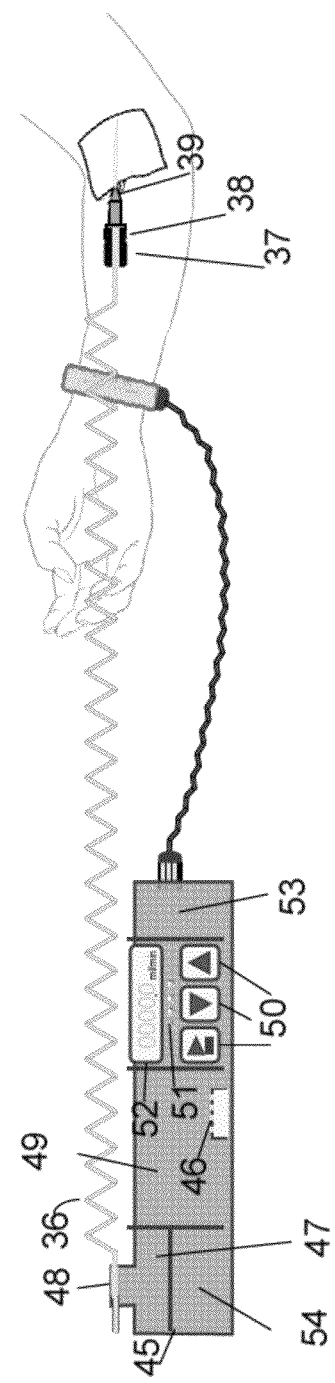
Figure 12D:
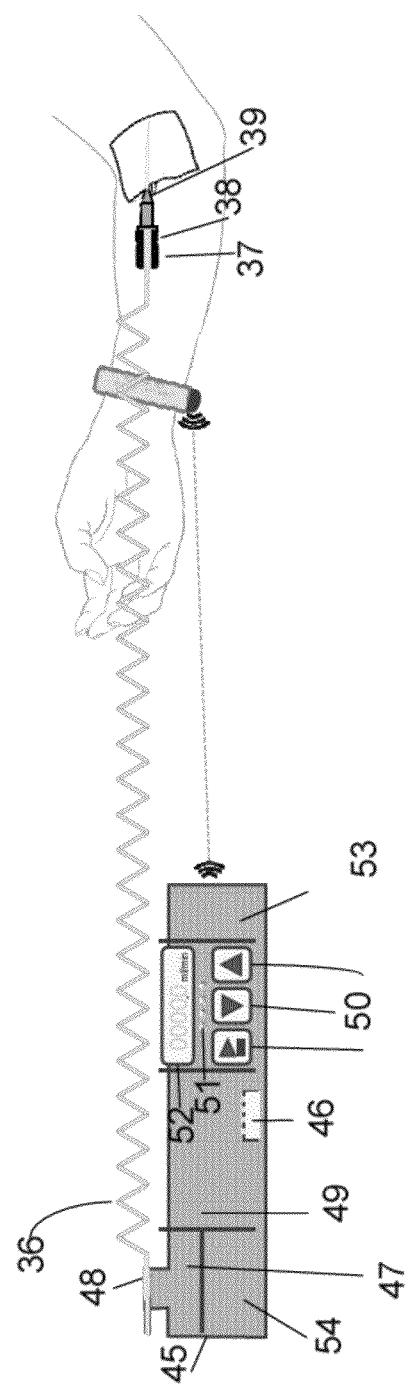

In an embodiment, the electronic control module 45 contains a system for positively identifying the patient. Such a patient identification system may use, as shown in FIG. 12C, a wired technology such as a flash memory electronic key 44, whereby a unique such electronic key 44 attached to the patient (e.g. neckstrap, wriststrap) is inserted into a connector on the electronic control module 45 which reads the patient information from the key 44. Alternatively, the patient identification system may use, as shown in FIG. 12D, wireless technology such as radiofrequency identification (RFID) technology, whereby an RFID reader/receiver 45 in the electronic control module receives a signal from a unique passive RFID transmitter 46 incorporated into the patient's identification tag (e.g. wristband), the connector on the patients infusion catheter or implanted infusion port. Having the RFID transmitter incorporated into and long-term infusion catheter or implanted port may be particularly attractive as it is inexorably, physically linked to the patient during the period of time the patient requires infusion therapy. In an embodiment, the long-term catheter or implanted infusion port may contain a pressure sensor which can transmit additional data such as the catheter/port characteristics and the patient's venous pressure along with the patient identification to the electronic control module 45 to incorporate into the infusion algorithm.

The rate of flow of the adjustable-rate, programmable infusion device may be controlled using a "digitized infusion" algorithm, whereby fixed microbolus volumes of the substance are infused at a given frequency to achieve the desired flow rate. Each microbolus volume may be delivered by opening the binary valve mechanism for a fixed period of time, during which the substance may be infused at the maximum flow rate of vessel. The microbolus volume v is $$v = Q_{max} t$$

Where Qmax is the maximum flow rate of the vessel and t is the duration of the microbolus. To achieve a desired flow rate Q, the microboluses are administered at a frequency f $$f = \frac{Q}{v} = \frac{Q}{Q_{max} t}$$

To achieve this frequency the binary flow valve 47 will alternate between open and closed states for $t_{open}$ and $t_{closed}$ as follows $$t_{open} = t$$
$$t_{closed} = \frac{1}{f} - t = \left(\frac{Q_{max}}{Q} - 1\right) t$$

In another embodiment, the device of the present disclosure (not shown) may include a stand-alone electronic control module 45 designed to be used with a conventional infusion system 47 (hanging IV bag, electric or disposable infusion pump) to provide some of the patient safety features of the infusion device of the present invention. In this embodiment, the primary purpose of the stand-alone electronic control module 45 is to identify the patient and permit or prevent flow from the convention infusion system depending on whether a match is confirmed. The device may be programmable, but not rate-adjustable as the flow rate of the infusion is determined by the conventional infusion system 47. The device may be provided with a disposable length of specialized tubing 48 similar to the integrated tubing 36 in the full device, which includes a interfacing segment 49 designed to interact with the binary flow valve 47 of the electronic control module 45. The tubing may be provided with a variety of proximal connectors 50 (e.g. luer lock, spike) to attach to conventional intravenous tubing 51 emanating from the conventional infusion system 47 and distal connectors 52 (e.g. luer lock, needle, needleless hub) to attach to the patient's infusion catheter or port. The binary flow valve 47 of the electronic control module 45 may be closed in the default state, occluding flow from the conventional infusion system 47. The electronic control module 45 may include a wired patient identification system such as an electronic key 44 attached to the patient which is connected to it or wireless patient identification system such as an RFID reader/receiver 45 which receives a signal from a unique passive RFID transmitter 46 attached to the patient. The patient identification system may determine whether the patient is the one for whom the infusion is intended. If a match occurs the binary flow valve 47 of the electronic control module 45 opens and allows the conventional infusion system 47 to proceed according to its own settings. If there is no match then the binary flow valve 47 may remain in its default closed position and the infusion cannot proceed. By providing patient identification functionality in a simple, compact, single- or multi-use disposable stand-alone electronic control module, the device of the present disclosure may improve the safety of existing conventional infusion devices.

In another embodiment, as shown in FIG. 13, the infusion device of the present disclosure may be capable of handling multiple, simultaneous, independently adjustable infusions. Such an infusion device may include a docking tray 53 with multiple slots 54 into which one or more of the above vessels 11 can be docked. The docking tray may have several (e.g. 2-5) separate outflow paths 55 each communicating with one lumen of a multi-lumen integrated tubing 56. In an embodiment, the docking tray 53 may have one dedicated infusion vessel which infuses a carrier fluid (e.g. saline, dextrose) at a low constant flow rate into all of the outflow paths 55.

The multi-infusion docking tray electronic control module 57 may include a linked series of individual vessel electronic control modules 45 similar to those previously described, each with its own binary flow valve, control circuitry, memory chip reader, switches, indicators, displays, etc. A central electronic control module 57 may include a common wired or wireless patient identification system, circuitry which communicates with the individual vessel modules, its own binary flow valve (to control the carrier fluid), switches, indicators, displays, etc. The central module may determine whether the individual vessel infusions can proceed based on whether the patient identification system confirms a match.

The fluid from each vessel 11 may be directed into one of the outflow paths 55 based on known drug-compatibility data. The device can achieve this manually or automatically. In an embodiment, each slot in the docking tray may have a manual switch which allows the operator to direct the fluid from the vessel 11 into the appropriate outflow path 55. In another embodiment, this process may be handled automatically. The electronic control module 45 for each vessel may have one binary flow valve for each outflow path 55. In an embodiment, the central electronic control module 57 may tell each vessel's electronic control module 45 which binary flow valve to open, routing compatible drugs into the same outflow path 55.

In an embodiment, a method is provided for preparing and using the infusion device of the present disclosure to deliver drugs and/or fluids to a patient. In an embodiment, a fixed-rate, non-programmable device of this invention may be prepared by the manufacturer or commercial pharmacy. The appropriate size and shape vessel 11 may be selected. Generally, the bottom wall 15 of the vessel 11 may be removable so that the various internal components can be assembled.

For a given infusion type, a limited range of vessel sizes may generally be provided. For example, for an intravenous infusion device the portfolio may include a series of vessels with fluid chamber 26 volumes similar to commonly available intravenous fluid bags (e.g. 50 ml, 100 ml, 250 ml, 500 ml, 1000 ml). For a vessel 11 of a given size, a range of maximum flow rates may be provided to accommodate the demands of different clinical scenarios. For example a vessel 11 with 1000 ml of fluid designed for rapid infusion over several minutes during a trauma resuscitation may be provided with a maximum flow rate of 500 ml per minute while another designed for a maintenance fluid infusion over several days may be provided with a maximum flow rate of 0.3 ml per minute.

In an embodiment, the maximum flow rate for a vessel 11 of a given design (size, shape, gas compression ratio) may be primarily determined by the characteristics (shape, permeability) of the variable flow resistor 28 contained within the outflow septum 17. In order to simplify manufacture and assembly, in an embodiment, the outflow septum 17 may be created separately and inserted into a slotted, gasketed channel in the vessel 11. That way a vessel 11 of a given size can be married to a specific outflow septum 17 with a given variable flow resistor 28 design to achieve the desired maximum flow rate. Using the above example, a single 1000 ml vessel 11 can be provided along with two different outflow septa 17. A first outflow septum 17 may include a highly permeable variable flow resistor 28 that, when used with this vessel 11, can provide high flow rates for the trauma resuscitation application. A second outflow septum 17 may include a less permeable variable flow resistor 28 that, when used with the same vessel 11, can provide low rates for the maintenance fluid application.

In an embodiment, a fully charged empty infusion device may be assembled, as shown in FIG. 5A. The appropriate vessel 11, outflow septum 17, gas vessel 29 and plunger system 23 may be selected. The outflow septum 17 may be inserted into its slotted, gasketed channel of the vessel. The gas vessel 29 may be inserted into the main chamber 12 followed by the plunger system 23. The plunger extension 25 may be inserted into the inner outflow channel 19. As shown in FIG. 4a, the gas vessel 29 may be bound to the main plunger 24 and provided as a single piece. The bottom wall 15 may further be attached completing the assembly.

The gas vessel 29 can be filled with gas 28 in one of several ways. In an embodiment, the gas vessel 29 may be provided prefilled and sealed with the final amount (mass mg as shown above) of gas 28. At atmospheric pressure, the prefilled gas vessel 29 may have a significantly larger volume than the main chamber 12 of the vessel 11. A compressing force may be applied to the gas vessel 29 and attached plunger system 23 as it is inserted into the main chamber 12. The application of the force may be continued until the bottom wall 15 is secured to the vessel.

In another embodiment the gas vessel 29 may be provided empty or partially filled, so that it can be inserted into the main chamber 12 along with the plunger system 23 without compression. After the bottom wall 15 is attached, the gas vessel may be filled with the remaining amount of gas 28 through an inlet port 33.

Next, the infusion device with the empty but charged vessel 11 maybe filled with the appropriate carrier fluid (e.g. saline, dextrose solution) while removing substantially all air from the vessel and tubing. This can be done through an inlet port 33 which communicates with the fluid chamber 26. The fluid of course may be infused under pressure to drive the plunger 22 into the pressure chamber 27, compressing the gas 28 in gas vessel 29 to a final pressure of P0. If a drug is being infused, the pharmacy staff at a commercial or hospital pharmacy can take the filled and charged vessel and inject a small-volume aliquot of the concentrated drug into the vessel, resulting in final concentration of drug within the vessel consistent with the physician's order. A label with the relevant patient, drug and infusion data, in human and, optionally, machine readable (e.g. bar code) form, may be permanently affixed or directly printed on the outside of the vessel.

The device may be delivered from the pharmacy to the patient, who may be at a hospital, non-hospital facility or at home. The nurse or other appropriately trained person, including the patient himself, may receive the device and confirm that it is the correct infusion for that patient. This can be done by visually comparing the information on the vessel label with that on a matching patient identification tag (e.g. badge, wristband). Alternatively, machine readable (e.g. bar code) data on the vessel label and patient identification tag can be compared by a handheld reader (e.g. bar code reader). Once an appropriate match is confirmed, the operator can simply connect the terminal connector 37 on the integrated tubing 36 to a provided matching connector attached to a infusion catheter or implanted infusion port already in the patient. In an embodiment with the drug/fluid in the device is already pressurized, the infusion may begin as soon as the connection is made and continues at a constant flow rate until the vessel is empty or the connectors are disengaged.

In another embodiment, a method is provided for delivering drugs and/or fluids to a patient using an adjustable-rate, programmable device of the present disclosure. In an embodiment, the non-volatile memory chip on the vessel 11 and the separate electronic control module 45 may be provided. The device may be assembled, pressurized, filled with carrier fluid and de-aired by the manufacturer, commercial pharmacy or central hospital pharmacy in the same fashion as above. If indicated, the appropriate amount of concentrated drug may be added by the pharmacy staff according to the physician's orders as above. A label with the relevant patient, drug and infusion data may be placed on vessel as above.

The vessel's non-volatile memory chip 44 may then be connected to a pharmacy computer through its electronic lead/connector 46. The computer may include a comprehensive drug/fluid database, complete infusion data (rate range, volume, time, etc.) and all relevant patient information (including but not limited to unique patient identification, clinical history, current kidney/liver function, known adverse drug reactions and current medications). Once the computer confirms that the infusion of the specified drug/fluid in the specified fashion is safe for the specified patient, the computer can store the appropriate patient and infusion data in the non-volatile memory unit 35 of the vessel 11.

An appropriate electronic control module 45 may then be selected and attached to the vessel 11 with the binary flow valve 47 in contact with the specialized segment 48 of the vessel's integrated tubing 36. The electronic control module 45 may also be in electrical contact with the non-volatile memory chip 44 through its lead/connector 46.

The completed infusion device, filled, charged, de-aired, labeled and programmed, may be then delivered from the pharmacy to the patient, who again may be at a hospital, non-hospital facility or at home. The nurse or other appropriately trained person, may connect the terminal connector on the tubing to a provided matching connector applied to a infusion catheter or implanted infusion port already in the patient. A match between the infusion device and the patient can first be manually confirmed by the operator, as above, by visually comparing the vessel label to the patient's identification tag. At the same time, the electronic control module 45 may confirm a match automatically using its patient identification system. If the electronic control module 45 uses a wired system, the patient's unique electronic key 44 may be inserted into the electronic control module 45 and its microprocessor circuitry 49 reads the patient information from the key. If the electronic control module 45 uses a wireless system, a passive RFID transmitter 46 incorporated into the patient's identification tag or infusion catheter/port digitally can transmit the patients identification information to the RFID reader/receiver 45 in the electronic control module 45.

The operator can then connect the terminal connector 37 on the integrated tubing 36 of the vessel 11 to a provided matching connector attached to a infusion catheter or implanted infusion port already in the patient. The operator can then press the "Run" button on the electronic control module 45. If the module confirmed a match through its patient identification system, the module 45 can open the binary flow valve 47 and permit the infusion to proceed at the programmed rate. If the module 45 does not confirm a match, the valve remains closed, the infusion is not permitted to proceed and the operator is notified of the error by illuminating a LED-type indicator, generating an audible error signal or by displaying an error message on and LED/LCD display 52.

If the infusion device is programmed by the pharmacy to be rate-adjustable, the operator may increase or decrease the infusion rate within a programmed range by pressing an "Up" or "Down" on the electronic control module 45. The electronic control module 45 may change the flow rate using the digitized infusion algorithm by increasing or decreasing the frequency of the microbolus volume infusions. As previously described, each microbolus volume may be delivery by opening the binary flow valve 47 for a fixed period of time. As the flow rate is being adjusted by the operator, the electronic control module 45 may indicate the current flow rate on the LED/LCD display 52. In an embodiment, if the flow rate is already at the programmed maximum (minimum) flow rate the "Up" ("Down") button will have no effect. The LED indicators or LED/LCD display 52 may notify the operator that the maximum or minimum flow rate had been reached. The device may include a soft override button, permitting the operator to increase or decrease the flow rate within a broader secondary programmed range. In an embodiment, the module 37, however, may prevent the operator from changing the rate to a value beyond some predetermined, programmed range based on the safety profile of the drug/fluid. The infusion may continue at the designated flow rate until the vessel is empty, the connectors are disengaged or the operator presses the "Pause" button.

In another embodiment, a method is provided for delivering drugs and/or fluids to a patient using a conventional infusion system 47 with a stand-alone electronic control module 45 of the present disclosure. The conventional infusion system 47 may be prepared by the pharmacy and nursing staff according to the physician's order. For example in the case of a simple gravity driven infusion, an appropriate amount of the prescribed drug may be injected into an IV bag with a given volume of the appropriate carrier fluid to achieve the desired concentration. The staff may select an appropriate stand-alone electronic control module 45 which may be connected to the pharmacy computer and programmed with the appropriate patient and infusion data as above. The staff may then select the appropriate disposable length of specialized tubing 48 along with the correct proximal connector 50 (in this case IV bag spike) and distal connector 52. The specialized tubing 48 may be connected to the IV bag and a small amount of fluid is allowed to flow through it to de-air it. The programmed stand-alone electronic control module 45 may be then latched onto the tubing so the interfacing segment 49 of the specialized tubing 48 lies within the binary flow valve 47 of the electronic control module 45.

The assembled infusion device may then be delivered to the patient. The operator can connect the distal connector 52 to a matching connector on the patient's infusion catheter or port and initiate the conventional infusion system, in this example by simply hanging the IV bag on a pole. If a wired patient identification system is used, the patient's unique electronic key 44 may be inserted into the electronic control module 45 and its microprocessor circuitry 49 may read the patient information from the key. If the electronic control module 45 uses a wireless system, a passive RFID transmitter 46 incorporated into the patient's identification tag or infusion catheter/port digitally may transmit the patients identification information to the RFID reader/receiver 45 in the electronic control module 45. When ready, the operator may press the "Run" button on the electronic control module 45. If the electronic control module 45 confirms a match, it can open the binary flow valve 47 and permits the infusion to proceed at the rate determined by the conventional infusion system 47 (in this example, by gravity). If it does not confirm a match, the binary flow valve 47 may remain closed, the infusion is not permitted to proceed and the operator is notified of the error by illuminating a LED-type indicator, generating an audible error sound or by displaying an error message on and LED/LCD display 52.

In another embodiment, a method is provided for simultaneously infusing multiple drugs/fluids into a patient using the multiple-infusion docking tray and multiple individual vessels containing the individual drugs/fluids. The docking tray 53 with its dedicated carrier fluid vessel may be prepared by the manufacturer, commercial pharmacy or hospital pharmacy by loading the charged vessel with the appropriate carrier fluid (e.g. saline, dextrose solution) while removing substantially all air from the vessel, the multiple outflow paths 55 and multi-lumen integrated tubing 56. The pharmacy staff may then select the appropriate filled, de-aired and charged docking tray 53 along with a separate filled, de-aired and charged vessel 11 for each initial drug to be infused. A small-volume aliquot of the each concentrated drug may be injected into its respective vessel, resulting in final concentrations of each drug consistent with the physician's orders.

The docking tray and each vessel may then be connected to the pharmacy computer containing a comprehensive drug/fluid database, infusion data for each drug and all relevant patient information. Once the computer confirms that the infusion of each drug/fluid in the specified fashion is safe for the specified patient, the computer may store the appropriate patient and infusion data in the non-volatile memory unit of the docking tray 53 and each vessel 11. An appropriate multi-infusion docking tray electronic control module 57 may be selected and the multi-infusion device may then be completed by connecting it to the prepared and programmed docking tray. A label with the relevant patient, drug and infusion data, in human and optionally machine readable (e.g. bar code) form, may be affixed or printed on the outside of the docking tray and each vessel 11.

The prepared docking tray 53 with its attached electronic control module 57 and the individual prepared vessels 11 may then be delivered to the patient's bedside. The bedside operator may first connect the multi-lumen integrated tubing 56 from the docking tray to the respective ports on the infusion catheter already in the patient. If a wired patient identification is being used, the operator may insert the unique patient electronic key 44 into the appropriate connector on the docking tray electronic control module 57. The operator may press the "Run" switch on the docking tray electronic control module 57 and if a positive patient identification has been confirmed using the wired or wireless system, the infusion of the docking tray carrier fluid at its fixed rate may be initiated. The operator may then dock each vessel 11 into an appropriate slot 54 in the docking tray. The electronic control module 57 may detect the vessel 11 and read the patient and infusion data from the vessel's memory unit 35. The electronic control module 57 may compare the patient information on the vessel's non-volatile memory unit 35 to that on the docking tray's memory unit to confirm positive patient identification. The operator may hit the "Run" button for that slot 54 on the docking tray electronic control module which opens the binary flow valve 47 for that slot, allowing that infusion to proceed.

In one embodiment the operator may be provided with a choice for each slot of inserting the vessel to communicate with one specific outflow path 55 in the docking tray 53. The operator may choose the slot to assure that only compatible drugs are sharing the same outflow path. In another embodiment, the control module 57 may be capable of routing each infusion into a specific outflow path 55 and does so based on stored drug compatibility data.

If the infusion from a given vessel is adjustable, the operator may be able to adjust the flow rate within the ordered/programmed range by pressing the "Up" and "Down" buttons on the control module 57 that corresponds with the slot 54 on the docking tray.

When the vessel 11 is empty, the vessel 11 may be removed and, if the infusion of that drug is to be continued, the vessel 11 may be replaced by a new filled, charged, de-aired and programmed vessel 11. If a new drug is prescribed, an individual vessel 11 for that drug may be prepared and programmed at the pharmacy and delivered to the patient's bedside. The operator may simply insert the vessel into an empty slot on the docking tray 53 and presses "Run". The docking tray electronic control module 57 may read the patient information on the non-volatile memory unit 35 of the new vessel 11 and may compare it with from the docking tray's non-volatile memory unit 35 which had been previously matched to the patient through the wired or wireless patient identification system. Assuming a positive identification has been confirmed, the new infusion may begin into the appropriate outflow path 55, determined by the operator or automatically by the control module. The system may permit vessels containing certain emergency drugs (e.g. pressors) to be available in code carts or in the unit's medication room, fully filled, charged and ready to be used but without the specific patient information. The control module of the docking tray can allow vessels containing these drugs to proceed, under well defined circumstances (e.g. operator override) for a limited time period, without requiring patient identification.

In another aspect, a method for optimizing the mechanical variable flow resistor is provided. As noted above, the balance of forces equation for all forces acting on the plunger with, positive defined as acting to the right, can be presented as following in equation (1): $\pi R^2 P_1 \mp F_{friction} - F_{spring} - \pi R^2 P_2 = 0$, where R is radius of the plunger, P1 and P2 are pressures on each side of the plunger. According to Equation (1), with a decreasing pressure driving this system, the plunger may monotonically be moving to the left Further, $F_{spring}$ may be determined from Hooke's law, which is presented in equation (2) as follows: $F_{spring} = k(D+x)$, where D is the amount the spring has been pre-compressed and x is the amount the plunger has to move to cover the inlet pressure. The frictional force can be found from equation (3) as following: $F_{friction} = 2\pi RL\mu P_0$, where P0 is both a maximum drive pressure as well as a compliance pressure between the plunger and the wall and L is the total length of the plunger interaction with walls of the housing. Therefore Equation (1) can rearranged as presented in equation (4): $\pi R^2 P_1 - \pi R^2 P_2 = F_{spring} \pm F_{friction}$. The pressure difference, $\Delta P$, that drives the system by rearranging Equation (4) is presented in equation (5) as follows:

$$\Delta P = P_1 - P_2$$
$$= \frac{F_{spring} \pm F_{friction}}{\pi R^2}$$
$$= \frac{k(D+x) \pm \mu 2\pi RLP_0}{\pi R^2}$$
$$= \frac{kD}{\pi R^2}\left(1 + \frac{x}{D}\right) \pm 2\mu P_0 \frac{L}{H}$$

Assuming that the amount of pre-compression of the spring is such that D>>x and the spring term is greater than the friction term, Equation (5) can be simplified so to have the difference in pressure over the aperture as a constant as presented in equation (6):

$$\Delta P = \frac{kD}{\pi R^2}.$$

Equation (6) may now be used to estimate the performance of the system. Next, the assumption that the friction term is smaller than the spring term gives equation (7):

$$2\mu P_0 \frac{L_0}{R} << \frac{kD}{\pi R^2}\left(1 + \frac{x}{D}\right).$$

By rearrangement and a few steps of math, Equation (7) can simplify to:

$$\frac{2\mu \pi R P_0 L_0}{kD} << 1.$$

Equation (8) can be used to optimize the design of the system. For instance, it appears from equation (8) that it may be desirable to have a small radius plunger (R), a small compliance pressure ($P_0$), small plunger interaction length (L), and a spring with a large spring constant (k) and a large compression length (D).

While the invention has been described in connection with the specific embodiments thereof, it will be understood that it is capable of further modification. For example, the fluid within chamber 26 and gas within chamber 27 can each be stored in a cartridge designed to be situated within the respective chambers. In this way, once either the fluid or gas cartridge is substantially empty, the empty cartridge can be remove and disposed, and a new cartridge filled with the fluid or gas can be replaced in the respective chamber. Furthermore, this application is intended to cover any variations, uses, or adaptations of the invention, including such departures from the present disclosure as come within known or customary practice in the art to which the invention pertains.

What is claimed is:

1. A pressure regulator comprising:
   an inlet cavity;
   a housing in communication with the inlet cavity;
   a plunger movably disposed within the housing;
   an outflow cavity defined between a surface of the plunger and the housing;
   a channel for fluid communication between the inlet cavity and the outflow cavity and configured to maintain equilibrium of forces acting on each side of the plunger; and
   an outlet through which the fluid can be dispensed from the outflow cavity,
   wherein the channel includes a cannula having one set of perforations in communication with the inlet cavity and a second set of perforations in communication with the outflow cavity, so as to allow the fluid to flow from the inlet cavity into the outflow cavity,
   wherein the cannula is slidable relative to the plunger to change a number of perforations from the set of perforations which are exposed in the inlet cavity to vary the flow from the inlet cavity into the outflow cavity.

2. The pressure regulator of claim 1 further comprising a mechanism that acts to exert a force on the plunger to maintain the plunger substantially stationary in an equilibrium position.

3. A pressure regulator comprising:
   an inlet cavity;
   a housing in communication with the inlet cavity;
   a plunger movably disposed within the housing;
   an outflow cavity defined between a surface of the plunger and the housing;
   an outlet through which the fluid can be dispensed from the outflow cavity; and
   a channel for fluid communication between the inlet cavity and the outflow cavity, the channel being configured to vary a flow rate of the fluid between the inlet cavity and the outflow cavity to maintain a substantially constant pressure on the plunger as the force acting on the plunger decreases to maintain a constant flow rate from the outlet cavity through the outlet,
   wherein the channel includes a cannula having one set of perforations in communication with the inlet cavity and a second set of perforations in communication with the outflow cavity, so as to allow the fluid to flow from the inlet cavity into the outflow cavity,
   wherein the cannula is slidable relative to the plunger to change a number of perforations from the set of perforations which are exposed in the inlet cavity to vary the flow from the inlet cavity into the outflow cavity.

4. The pressure regulator of claim 3 further comprising a mechanism that acts to exert a force on the plunger to maintain the plunger substantially stationary in an equilibrium position.

* * * * *